(12) United States Patent
Shau

(10) Patent No.: US 10,744,391 B2
(45) Date of Patent: Aug. 18, 2020

(54) HANG TIME MEASUREMENTS USING WEARABLE ELECTRONIC DEVICES

(71) Applicant: David Shau, Palo Alto, CA (US)

(72) Inventor: David Shau, Palo Alto, CA (US)

(*) Notice: Subject to any disclaimer, the term of this patent is extended or adjusted under 35 U.S.C. 154(b) by 0 days.

(21) Appl. No.: 16/591,754

(22) Filed: Oct. 3, 2019

(65) Prior Publication Data
US 2020/0230486 A1 Jul. 23, 2020

Related U.S. Application Data

(63) Continuation-in-part of application No. 16/253,230, filed on Jan. 22, 2019, now Pat. No. 10,486,025.

(51) Int. Cl.
| | | |
|---|---|---|
| *A63B 71/06* | (2006.01) | |
| *A63B 69/12* | (2006.01) | |
| *A63B 69/00* | (2006.01) | |
| *A63B 69/18* | (2006.01) | |
| *A63B 24/00* | (2006.01) | |
| *A63B 33/00* | (2006.01) | |

(52) U.S. Cl.
CPC ...... *A63B 71/0622* (2013.01); *A63B 24/0062* (2013.01); *A63B 33/002* (2013.01); *A63B 69/0071* (2013.01); *A63B 69/12* (2013.01); *A63B 69/18* (2013.01); *A63B 2071/0625* (2013.01); *A63B 2208/03* (2013.01); *A63B 2220/40* (2013.01); *A63B 2220/836* (2013.01)

(58) Field of Classification Search
CPC ..... A42B 1/245; A42B 3/30; A63B 2033/004; A63B 33/002; G01P 5/00; G06F 3/167; H04R 3/00; G10L 13/02
See application file for complete search history.

(56) References Cited

U.S. PATENT DOCUMENTS

| | | | |
|---|---|---|---|
| 5,423,215 A * | 6/1995 | Frankel | G01C 5/00 244/147 |
| 5,838,638 A | 11/1998 | Tipton | |
| 7,379,842 B2 * | 5/2008 | Alexander | A63B 24/0021 702/160 |
| 7,650,257 B2 * | 1/2010 | Alexander | A63B 24/0021 702/150 |
| 8,108,177 B2 | 1/2012 | Alexander | |
| 10,156,830 B2 * | 12/2018 | Germiquet | A61B 5/681 |
| 2002/0116147 A1 * | 8/2002 | Vock | A63C 5/06 702/182 |
| 2006/0010587 A1 | 1/2006 | Yokota | |
| 2007/0061106 A1 * | 3/2007 | Vock | G01P 3/50 702/182 |
| 2010/0030482 A1 | 2/2010 | Li | |

(Continued)

*Primary Examiner* — Francis C Gray

(57) ABSTRACT

Wearable electronic devices that are designed to be worn on the head of a user while the user is swimming can determine swimming strokes and swimming performances of the user using motion sensors. Using a sound speaker, the wearable electronic device can play music and provide audio feedback to the swimmer. By comparing the swimming performance of the swimmer wearing the device with previously recorded swimming data, the wearable electronic device can provide audio comparison results to the swimmer while the swimmer is swimming in water. The wearable electronic device can also support similar functions for jumping actions.

12 Claims, 18 Drawing Sheets

(56) References Cited

U.S. PATENT DOCUMENTS

| | | | |
|---|---|---|---|
| 2014/0070957 A1* | 3/2014 | Longinotti-Buitoni | ........................ A61B 5/6804 340/870.01 |
| 2016/0059073 A1* | 3/2016 | Jeon | ........................ A63B 5/20 482/9 |
| 2017/0072283 A1* | 3/2017 | Davisson | ........... G09B 19/0038 |
| 2017/0196513 A1* | 7/2017 | Longinotti-Buitoni | ........................ A61B 5/6804 |

* cited by examiner

FIG. 5(b) (amended)
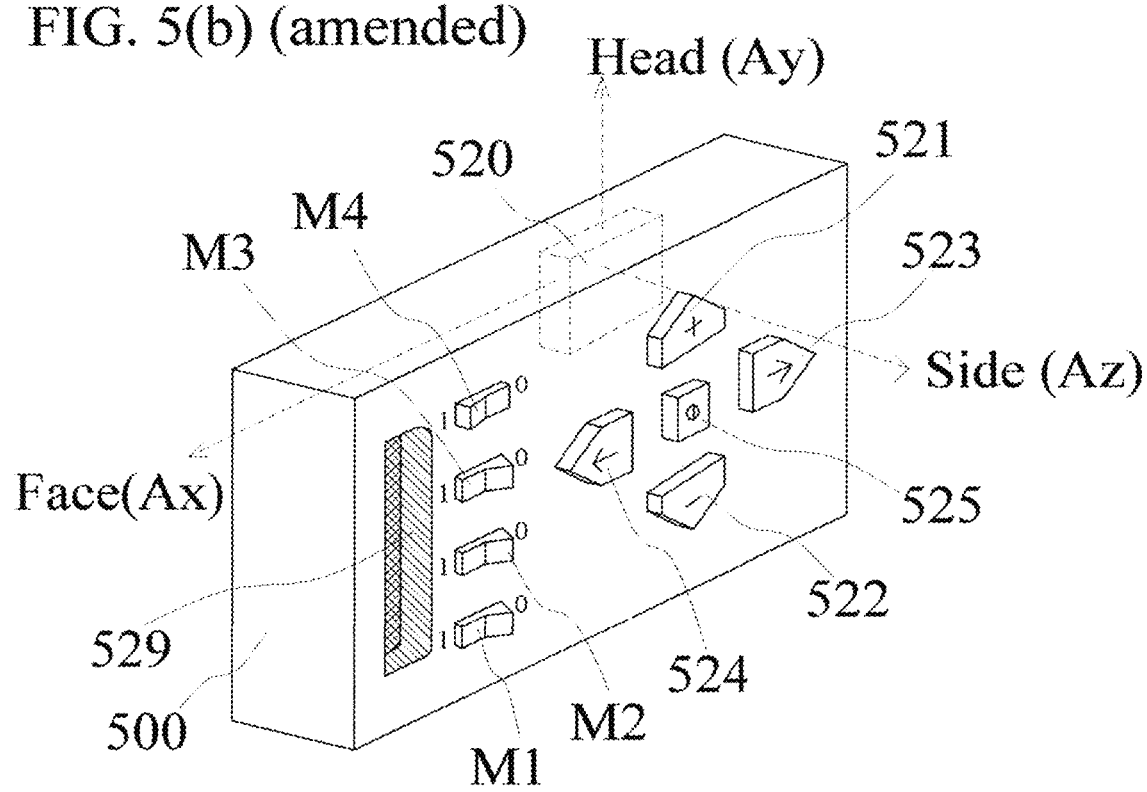

FIG. 5(g)

| M1 | M2 | M3 | M4 | Actions |
|---|---|---|---|---|
| 0 | 0 | x | x | Do nothing, power down |
| 0 | 1 | 0 | 0 | Play music |
| 0 | 1 | 0 | 1 | Play music while swimming |
| 0 | 1 | 1 | 0 | Synchronize music tempo to swimming pace |
| 0 | 1 | 1 | 1 | Adjust volume according to swimming speed |
| 1 | 0 | 0 | 0 | Lap count |
| 1 | 0 | 0 | 1 | Lap count + lap time |
| 1 | 0 | 1 | 0 | Lap count + lap time + stroke count |
| 1 | 0 | 1 | 1 | Report Calories burned |
| 1 | 1 | 0 | 0 | Lap count + music |
| 1 | 1 | 0 | 1 | Lap count + lap time + music |
| 1 | 1 | 1 | 0 | Lap count + lap time + paced music |
| 1 | 1 | 1 | 1 | Store data into memory |

FIG. 6(a)
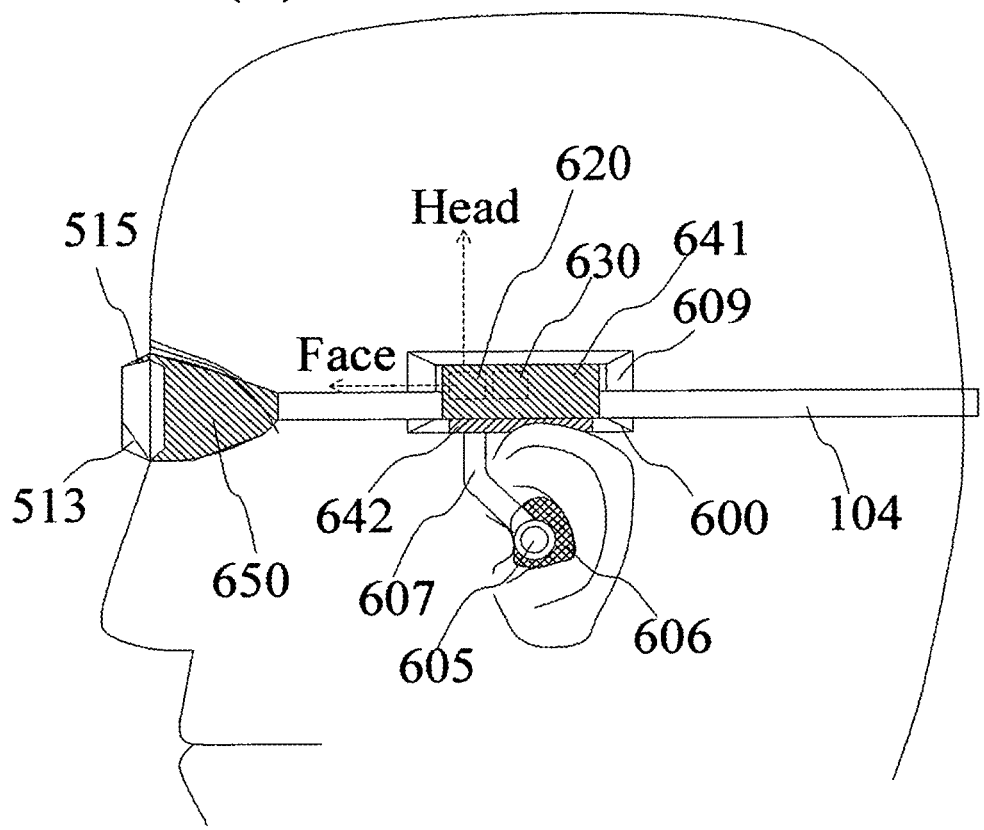
FIG. 6(b)
FIG. 6(c)
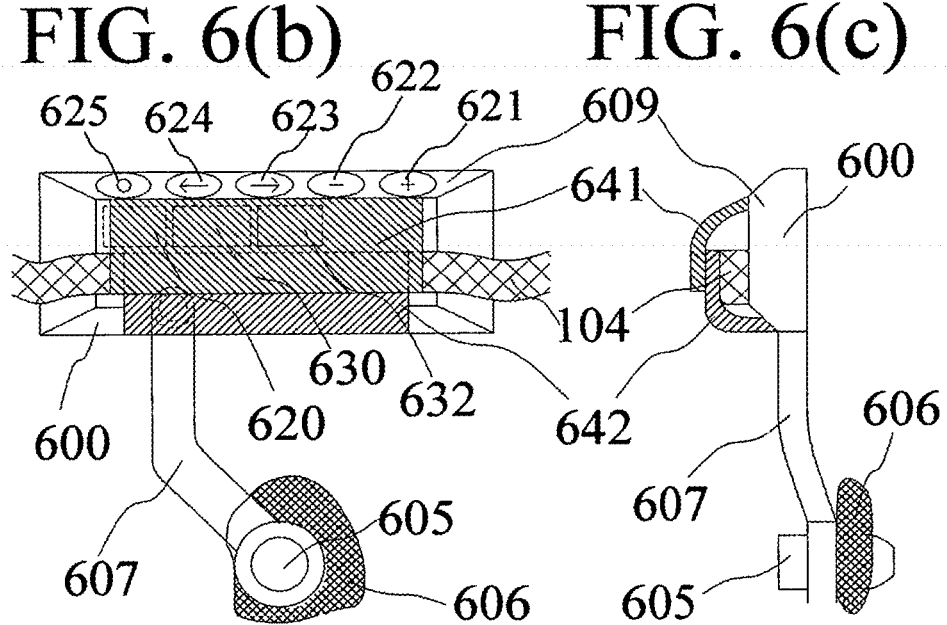

HANG TIME MEASUREMENTS USING WEARABLE ELECTRONIC DEVICES

This application is a continuation-in-part of the previous patent application with the Ser. No. 16/253,230, and with the title "Wearable Electronic Devices with Swimming Performance Comparison Capabilities," which was filed by David Shau on Jan. 22, 2019.

BACKGROUND OF THE INVENTION

The present invention relates to wearable electronic devices, and more particularly to wearable electronic devices that measure hang time and vertical jump height.

Swimming is a sport that keeps people in great shape. Swimming exercises most of the body's muscles, and swimming can even save one's life. For most of competitive sports, it is almost guaranteed that people will eventually get hurt by sport injuries. In comparison, swimming is a sport that rarely causes serious injury. However, like me, most swimmers have bumped their head at the end of the pool while swimming backstroke. While at full sprinting speed, this type of injury may even result in minor concussions, and is also quite painful. It is desirable to design swimming goggles that allow swimmers to see the end of the pool without moving their head while swimming in backstroke. Also, backstroke swimmers often swim in a curvy zigzag path in their lane instead of a simple direct straight line. If the swimmer swims in a zigzag path, then the distance that they swim will be longer, and it also makes them look bad. It is desirable for a swimmer to see the sights behind them while swimming backstroke, so that they may line up their position, thus allowing the swimmer to swim in a straight line. It is also desirable to have swimming goggles that can help swimmers maintain proper head position while swimming backstroke.

Li in US publication number 2010/0030482 disclosed devices that monitor the body orientation of a swimmer, and provide real time comparisons between the current performance of the swimmer and previously achieved performances of the same swimmer. However, Li's device does not measure the head orientation of a swimmer. Head orientation is significantly different from body orientation because the accelerations at the head of a swimmer are significantly different from the accelerations at the body of a swimmer. This is because head motions are very different than body motions when swimming, an idea that has been proven by experimental results. Furthermore, Li does not compare the results of different swimmers, does not adjust the reference data for different swimming conditions, and does not disclose comparisons with universally accepted swimming time standards.

The previous application with the Ser. No. 16/253,230 disclosed wearable electronic devices that provide feedback for the user's physical activities by using audio, changes in the music played, or goggle adjustments. Such devices also provide additional feedback to the user by comparing the user's current swimming performance with recorded, standardized swimming performances, or with recorded swimming performances of another swimmer. The previous application disclosed a method of using a near-zero-g condition as a component for detecting swimming dives performed by the swimmer, as well as for measuring detailed statistics about such swimming dives. The movement patterns of individuals during jumps are similar to those of swimming dives, but the algorithms used for detecting and analyzing jumps still differ from those used for detecting and analyzing swimming dives. This patent application discloses applications in jump detection and analysis.

As used herein, the terms "time of flight" and "hang time" are synonymous and refer to the length of continuous time that an object or individual is in the air without making contact with or being supported by a surface. This length of time starts at the point at which the object or individual jumps, takes off, or leaves a surface that is able to support the weight of the object or individual. This length of time ends at the point at which the object or individual lands, or makes contact with a surface that is able to support the weight of the object or individual. Furthermore, the word "jump" can refer to any sort of physical action that an individual enacts in order to make himself/herself airborne for a length of time. Finally, the terms "vertical jump height," "jumping height," and "jump height" are synonymous and refer to the distance from the center of mass of an individual when he/she is initially being supported by a surface just before takeoff to his/her center of mass when his/her center of mass is at its peak elevation during a jump.

Tipton et al. in U.S. Pat. No. 5,838,638 disclosed a portable vertical jump measurement device that uses a stepping pad that comprises electrical switches. Hang time is measured when the user jumps off of the stepping pad and consequently changes the states of electrical switches. Although functional, Tipton's device occupies significant amounts of surface area, and while the device can be considered portable, it certainly is not wearable. In addition, users must ensure that they start and end their vertical jumps on the stepping pad, which significantly limits when and where the users can measure their vertical jump statistics. These constraints render the device unusable for measuring jumps performed during physical activities or sports such as basketball, where lots of movement in open space is required. Furthermore, the device does not contain an electrical sound speaker that provides real time feedback immediately after the user jumps. Tipton's device also does not use an accelerometer.

Alexander in U.S. Pat. No. 8,108,177 disclosed a wearable electronic device that uses an accelerometer to measure the time of flight of a jumper that has jumped into the air. Alexander assumes that a jumper, such as a skier or snowboarder, will experience a static acceleration of approximately one g when the jumper is being supported by a solid surface, and about zero g when the jumper is not in contact with a solid surface, where one g is equivalent to approximately 9.8 meters per second squared. Using this assumption, Alexander measures hang time as the length of continuous time where the jumper's acceleration is approximately zero g. This assumption is true only when the jumper wearing the device does not make any significant movements while he/she is airborne. For example, Alexander's assumption does not hold when the jumper is rotating about any axis in the air; it also does not hold when the jumper makes sudden accelerations and movements while airborne either. This is because such rotations and sudden accelerations while airborne will be measured by the accelerometer, resulting in a non-zero g acceleration. Consider a snowboarder who performs a rotating flip in the air or a basketball player who executes rotations for a spinning dunk. In these situations, the users' jumps would not be detected or measured if Alexander's method were to be used, since their accelerations in the air would not be close to zero. Therefore, Alexander's method is impractical for measuring and detecting jumps in multiple realistic conditions. In addition, Alexander's devices do not comprise an electrical sound speaker that provides real time feedback to the user immediately after he/she performs a jump.

SUMMARY OF THE PREFERRED EMBODIMENTS

A primary objective of the preferred embodiments is, therefore, to provide swimming goggles that allow the user to see behind him or her without changing their normal head position while swimming backstroke. This will reduce the chance of injury, since they can now see where the wall is. Another objective is to prevent the swimmer from swimming in a zigzag manner when they swim across the pool in their lane. This will allow the swimmer to go faster, and prevent the user from crashing into the lane lines. Another primary objective is to provide sophisticated motion related information to a swimmer while the swimmer is swimming. Another objective is to provide feedback to the user by comparing his or her swimming performances to that of other swimmers, or to previous swimming performances of the same user. Another objective is to provide feedback to the user by comparing his or her athletic performances to that of other athletes. Another primary objective is to provide practical hang time measurements and statistics for users. Another objective is to provide real time feedback regarding such hang time measurements to users.

While the novel features of the invention are set forth with particularly in the appended claims, the invention, both as to organization and content, will be better understood and appreciated, along with other objects and features thereof, from the following detailed description taken in conjunction with the drawings.

BRIEF DESCRIPTION OF THE DRAWINGS

FIG. 5(b) shows a close up of the electric controller in FIG. 5(a);

FIG. 5(g) shows a table that lists exemplary modes supported by the electric controller in FIG. 5(c);

FIGS. 6(a-c) are simplified symbolic diagrams showing the structures of an exemplary electronic attachment for a swimming goggle;

DETAILED DESCRIPTION OF THE PREFERRED EMBODIMENTS

Figure 1A:
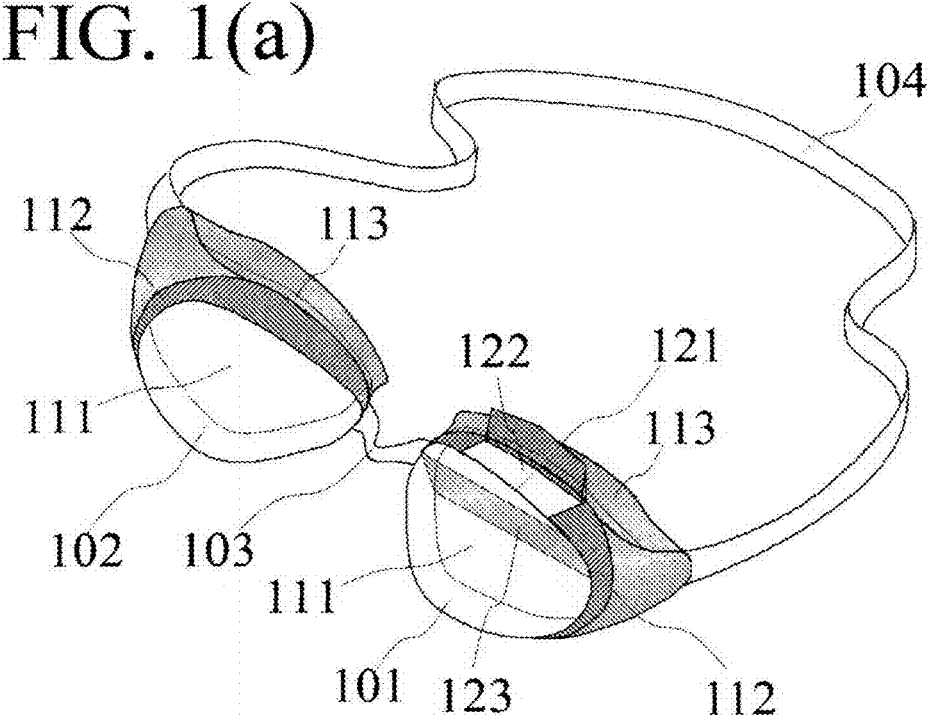
FIG. 1(a) shows one example of the swimming goggles of the present invention that has a backstroke viewing window on one eye socket.
Figure 1B:
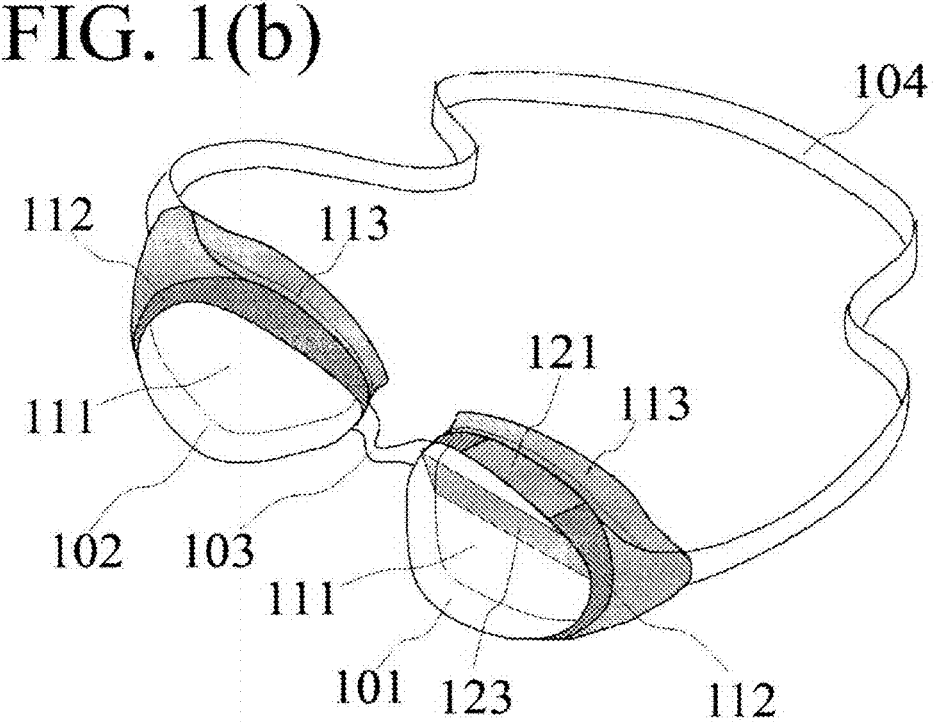
FIG. 1(b) shows the swimming goggle in FIG. 1(a) while the light blocking cover of the backstroke viewing window is closed.

FIGS. 1(a-d) show examples of the goggles of the present invention. The goggles in these examples comprise two eye sockets (101,102) connected by a nosepiece (103) and a head strap (104). Each eye socket (101,102) has a forward viewing window (111) that is mounted on a suction socket (113). Typically, the forward viewing window (111) is made of transparent plastic plate, and the suction socket (113) is made of rubber or plastic. The suction socket (113) sticks onto swimmer's eyes, creating a water tight seal while providing a space between the eye and the forward viewing window (113), allowing clear under-water vision. These structures are similar to those used in conventional swimming goggles. In addition, the examples in FIGS. 1(a-d) contain structures that are designed to allow the swimmer to see the end of the pool without moving their head while swimming in backstroke. For example, FIGS. 1(a, b) illustrate a goggle that has a backstroke viewing window (122) opened at the upper side (112) of the eye socket. A backstroke viewing window, by definition, is a transparent window on the eye socket of a swimming goggle that faces upward direction while the swimmer wearing the goggle is standing upright so that it faces the end of swimming pool when the swimmer is in normal head position while swimming backstroke. A backstroke viewing window is typically nearly vertical to the front viewing window. In this example, the backstroke viewing window (122) is made of transparent plastic. To prevent unwanted peripheral lights, the backstroke viewing window (122) can be covered with a light blocking cover (121). FIG. 1(a) illustrates the situation when the light blocking cover (121) of the backstroke viewing window (122) is opened, and FIG. 1(b) illustrates the situation when the light blocking cover (121) is closed. In this example, a light reflector (123) is placed inside the eye socket (101), as illustrated in FIGS. 1(a, b). In this example, the light reflector (123) is a transparent plastic plate supporting the functions of a half-mirror. A half-mirror, by definition, is a light reflector that is partially transparent and partially reflecting. In this example, the index of reflection of the light reflector (123) is adjusted in such way that the reflected view is more dominating than the transparent view. When the light blocking cover (121) of the backstroke viewing window (122) is opened, as shown in FIG. 1(a), the light that travels through the backstroke viewing window (122) is reflected by the light reflector (123), allowing the swimmer to see the end of the pool without moving head while swimming in backstroke. When the light blocking cover (121) of the backstroke viewing window (122) is closed, as shown in FIG. 1(b), almost no light would come from the upward direction so that the swimmer would see views at the front direction through the half-mirror light reflector (123).

While the preferred embodiments have been illustrated and described herein, other modifications and changes will be evident to those skilled in the art. For example, the light reflector (123) can be a mirror instead of a half-mirror. For another example, FIG. 1(c) shows another goggle that has a backstroke viewing window (124) without a light blocking cover. This goggle can be manufactured at lower cost, but users may see unwanted lights from upward direction. Another example in FIG. 1(d) shows a goggle with backstroke viewing windows (124, 125) and light reflectors (123, 126) in both eye sockets (101,102). This goggle allows better upward vision because both eyes are now able to see the same reflection, but front view will be less clear. It is to be understood that there are many other possible modifications and implementations so that the scope of the invention is not limited by the specific embodiments discussed herein.

Figure 2A:
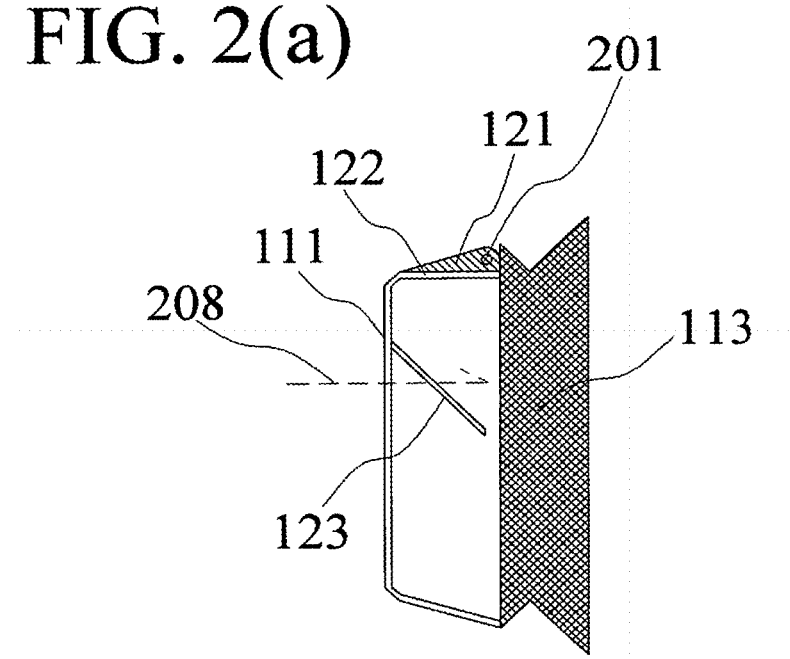
FIG. 2(a, b) are cross-section views of an eye socket that can automatically switch the position of the light blocking cover of the backstroke viewing window.
Figure 2B:
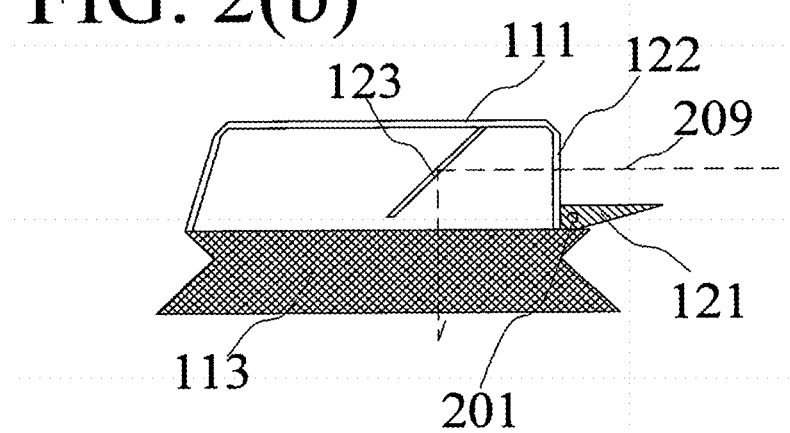
Figure 3A:
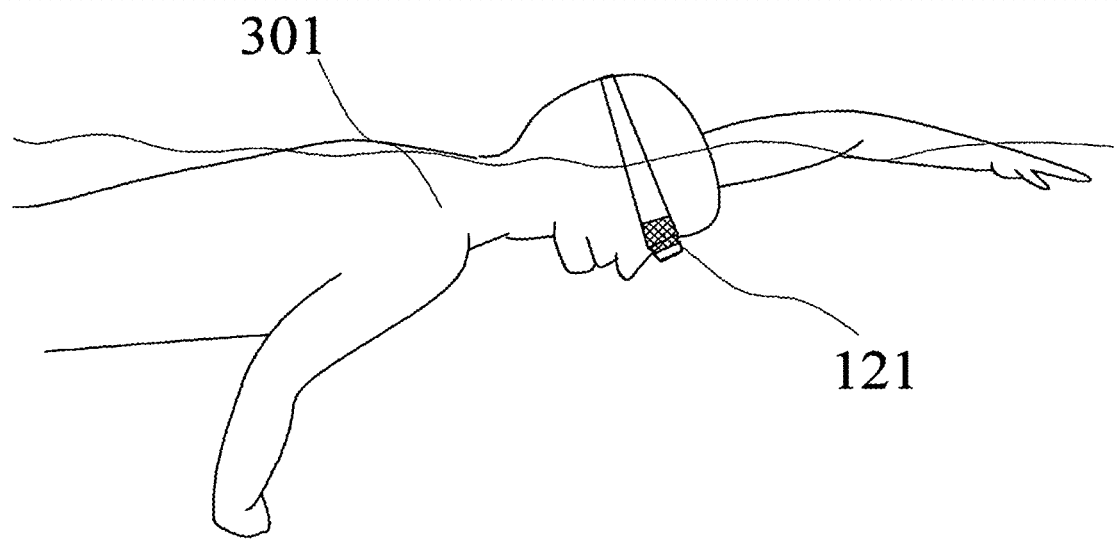
FIG. 3(a) shows a simplified view of a user who is swimming freestyle on his front.
Figure 3B:
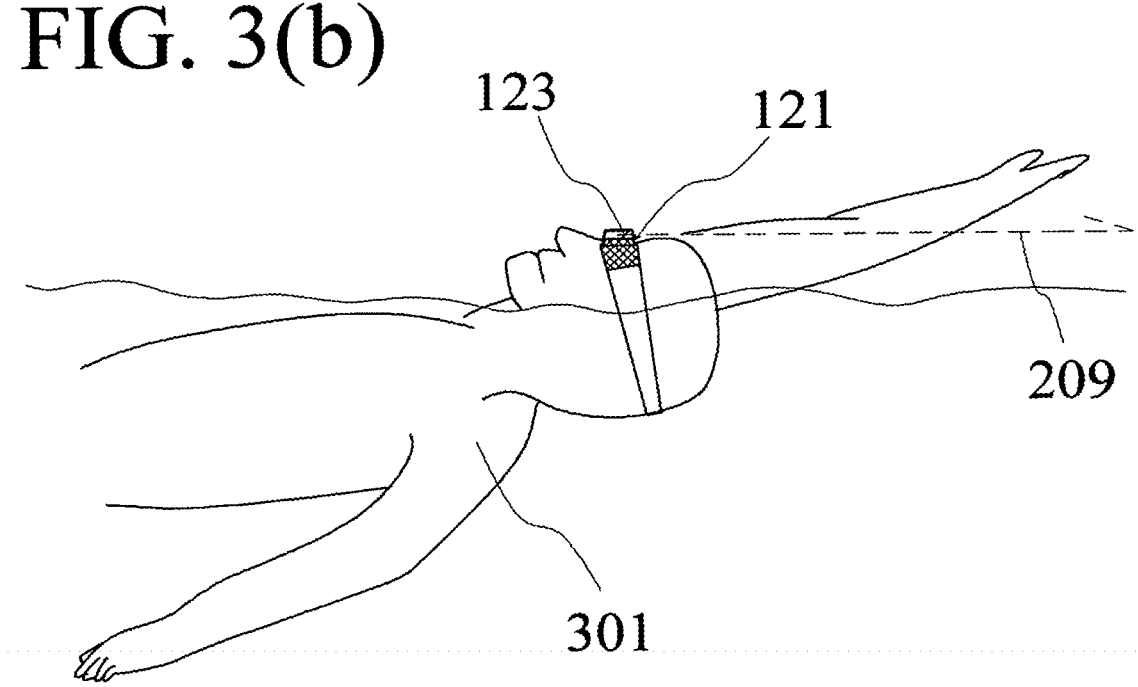
FIG. 3(b) shows a simplified view of a user who is swimming backstroke on his back.
Figure 3C:
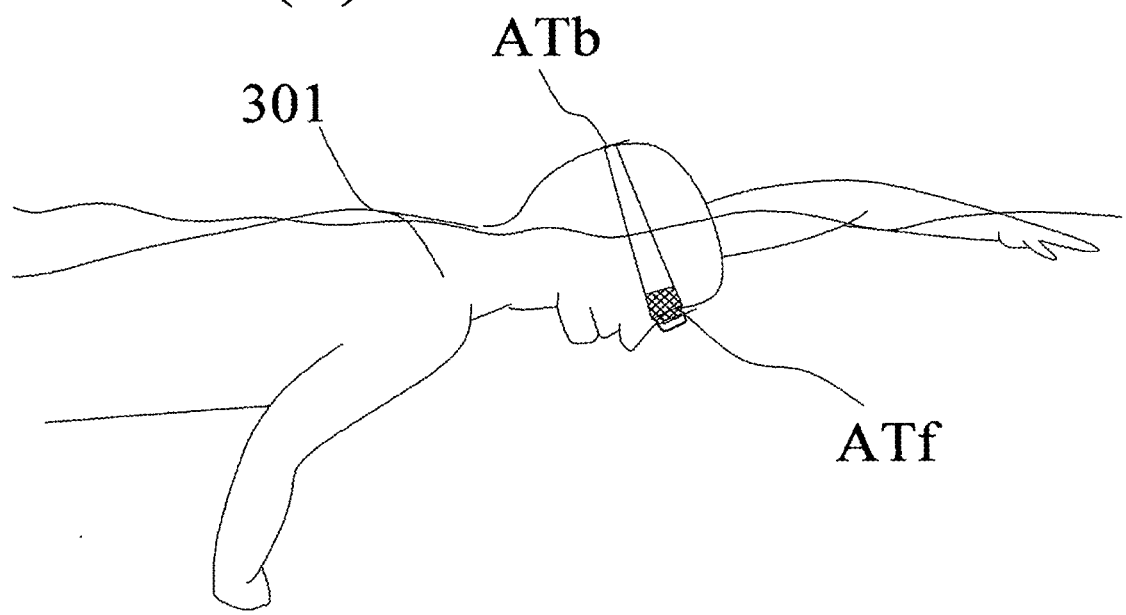
FIG. 3(c) shows a simplified view of a user who is swimming freestyle with his face facing towards the bottom of the pool while wearing an electronic device with two antennas.
Figure 3D:
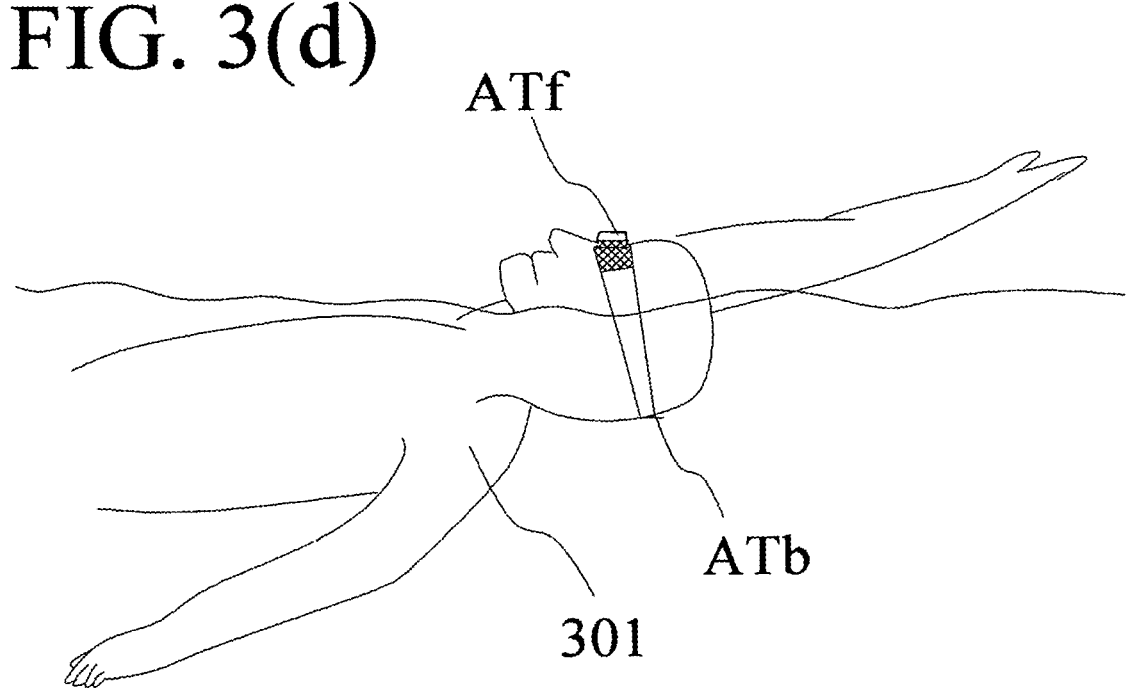
FIG. 3(d) shows a simplified view of a user who is swimming backstroke on his back facing towards the sky while wearing an electronic device with two antennas.

The light blocking cover (121) of the backstroke viewing window (122) shown in FIGS. 1(a, b) may be opened or closed manually. A swimmer can open the light blocking cover while swimming backstroke, and close it while swimming other strokes. While swimming melody, a swimmer needs to swim backstroke and other strokes. Flipping the light block cover while swimming can be troublesome. It is desirable to open or close the light blocking cover (121) automatically according to the stroke the swimmer is swimming. FIGS. 2(a-b) show cross-section views of an eye socket that can open or close the light blocking cover (121) automatically. In this example, the light blocking cover (121) is designed to rotate around a rotation axis (201). When the socket is at a position as illustrated in FIG. 2(a), the light blocking cover (121) is closed due to gravity. Under this situation, the light (208) passes directly through the half mirror (123) allowing the user to see what they would normally see while facing forward. Due to gravity, the light blocking cover (121) is also closed when the eye socket is facing downward. FIG. 3(a) illustrates the situation when a swimmer (301) wearing the goggle is swimming freestyle. Under this situation, the light blocking cover (121) of the backstroke viewing window is closed so that the swimming goggle functions as a conventional goggle. While swimming backstroke, the eye socket would face upward as illustrated by FIG. 3(b) and by the cross-section diagram in FIG. 2(b). At this position, the light blocking cover (121) would rotate backward along the rotation axis (201) by gravity, opening the backstroke viewing window (122) as illustrated in FIG. 2(b). The light (209) through the opened window (122) is reflected by the light reflector (123), allowing the swimmer (301) to see the end of the pool without moving his head while swimming in backstroke.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, the light reflector also can be automatically switched into position as shown by the cross-section diagrams in FIGS. 4(a-b).

Figure 4A:
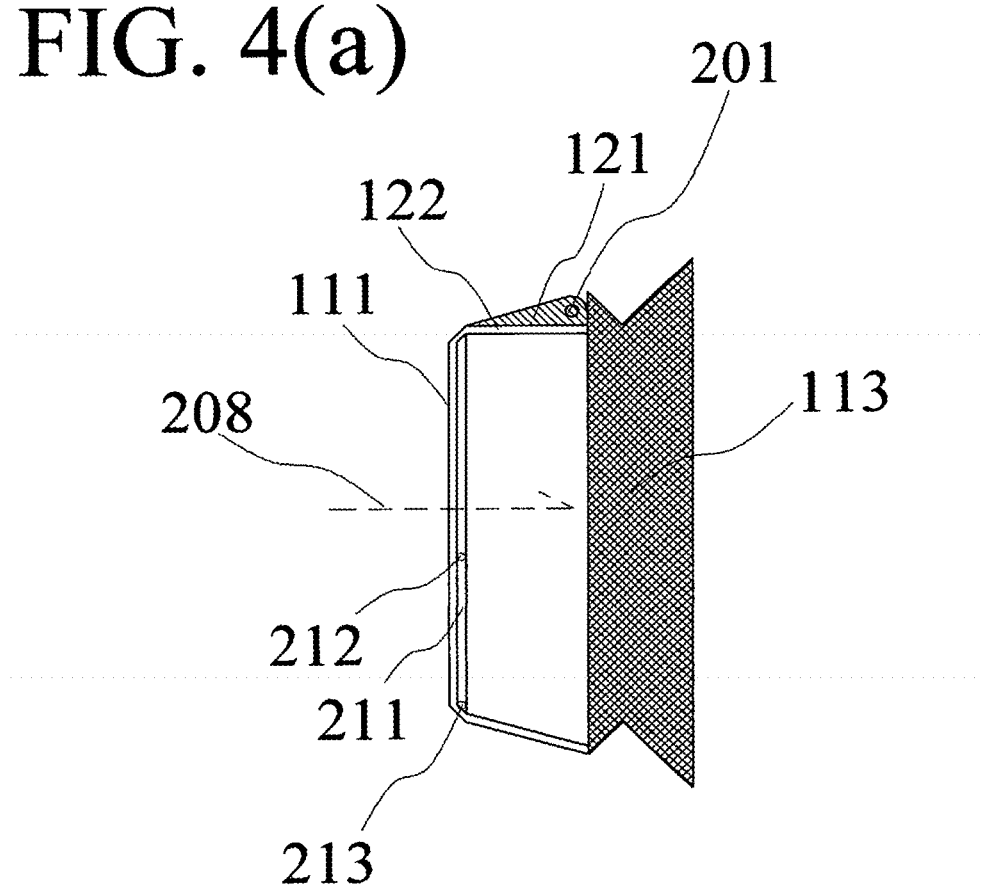
FIG. 4(a, b) are cross-section views of an eye socket that can automatically switch the positions of the light blocking cover and the light reflector.
Figure 4B:
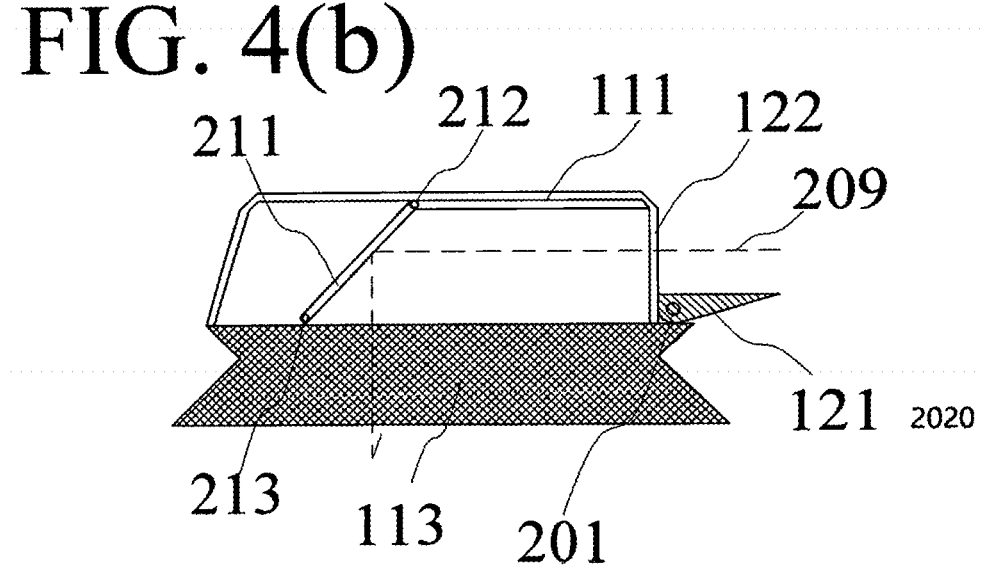

The eye socket shown in FIGS. 4(a-b) is similar to the eye socket shown in FIGS. 2(a, b) except that it has a light reflector (211) that can rotate against a rotation axis (212). A weight (213) is placed near the end of the light reflector (211) so that its position can be switched by gravity. When the socket is at a position illustrated in FIG. 4(a), the light reflector (211) is pulled by gravity to be in contact with the front viewing window (111) and functions as part of the front viewing window. Under this situation, the eye socket behaves as a conventional eye socket. Due to gravity, the position of this light reflector (211) would remain the same while the swimmer is swimming freestyle, breast, or butterfly strokes. While swimming backstroke, the eye socket would face upward, and the light reflector (211) would fall down due to gravity, as shown in FIG. 4(b). The light (209) through the opened backstroke viewing window (122) is reflected by the light reflector (211), allowing the swimmer to see the end of the pool without moving their head while swimming in backstroke.

The preferred embodiments of the present invention provide swimming goggles that allow the user to see the end of swimming pool without changing normal head position while swimming backstroke. The chance of injury is reduced because backstroke swimmers can now see where the wall is. The backstroke swimmer also can adjust swimming direction by vision to swim in straight line to achieve better time. These and other objectives are achieved by opening backstroke viewing windows at the eye sockets of swimming goggles. A light blocking cover can be used to prevent unwanted light going through the backstroke viewing window. The light blocking cover can be operated manually or automatically. A light reflector is typically used with the backstroke viewing window. This light reflector can be a half mirror or a full mirror. The light reflector also can be designed to change position automatically according the stroke the swimmer is swimming.

While the preferred embodiments have been illustrated and described herein, other modifications and changes will be evident to those skilled in the art. It is to be understood that there are many other possible modifications and implementations so that the scope of the invention is not limited by the specific embodiments discussed herein. While the examples in FIG. 4(a, b) automatically switch the position of the light blocking cover and the light reflector by gravity, we can also use the buoyant force of water, the body motions of the swimmer, and other methods to switch the positions of the light blocking cover or the light reflector. FIGS. 5(a-g) show an exemplary swimming goggle that switches the position of the light blocking cover and the position of the light reflector by an electric controller.

Figure 1C:
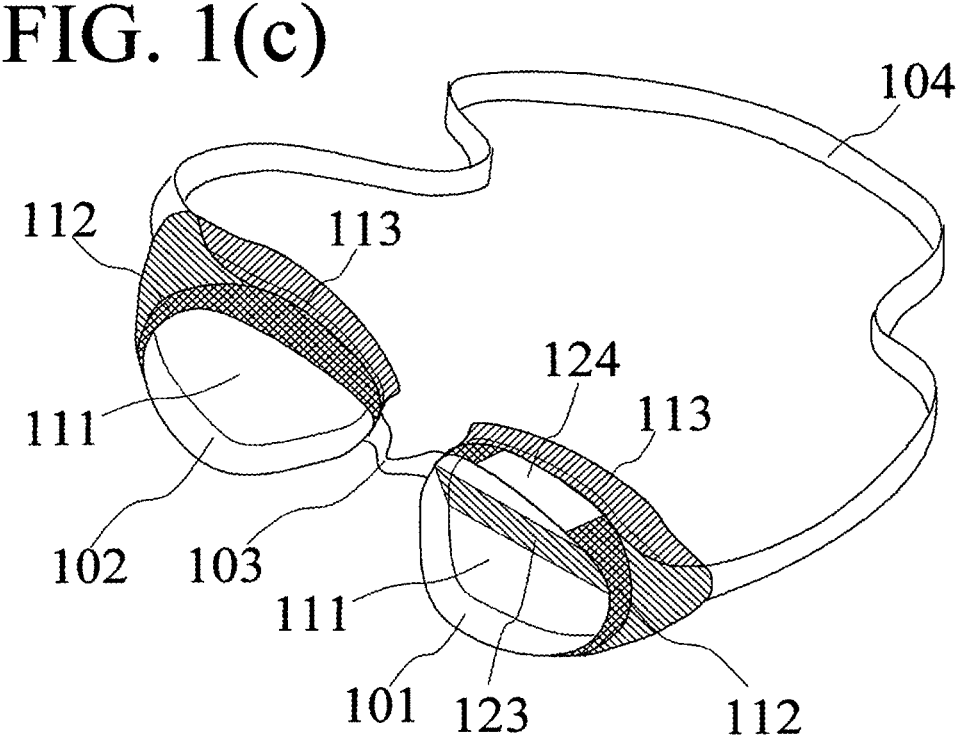
FIG. 1(c) shows a goggle without a light blocking cover on the backstroke viewing window.
Figure 1D:
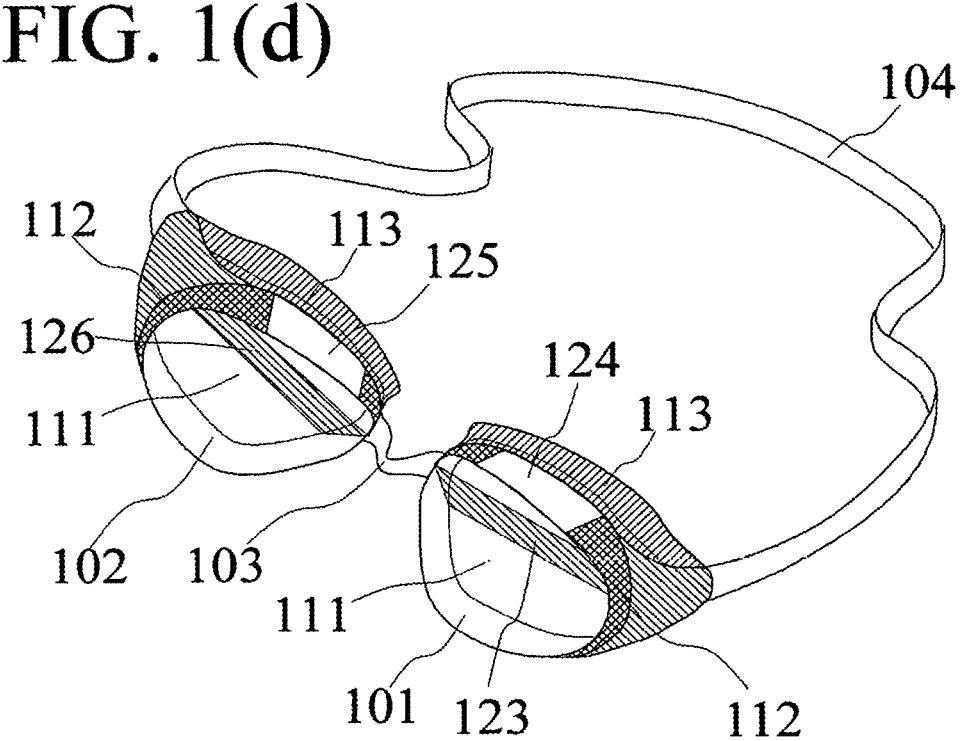
FIG. 1 (d) shows a goggle with backstroke viewing windows on both eye sockets.
Figure 5A:
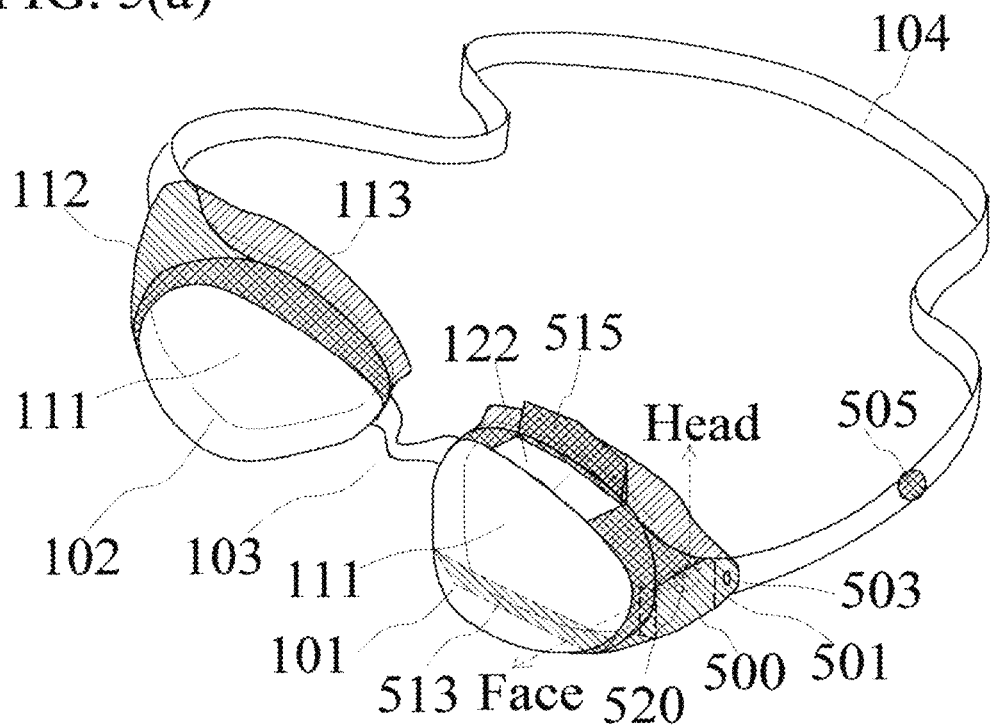
FIG. 5(a) shows a swimming goggle that has an electric controller (500) and an electric sound speaker (505)

FIG. 5(a) shows a swimming goggle that has the same structures as those of the swimming goggle in FIG. 1(a) except that the swimming goggle in FIG. 5(a) has an electric sound speaker (505) attached to its head strap (104), and an electric controller (500). This electric controller (500) is able to control the position of a light reflector (513) and the position of a light blocking cover (515). The electric controller (500) is covered by a water-tight cover (501) when the goggle is used in water. A button (503) on the water-tight cover (501) allows the user to open the cover in order to adjust operation modes of the electric controller (500). A motion sensor (520) is placed inside of the electric controller (500). This motion sensor (520) is attached to the swimming goggle at a fixed position with respect to the forward viewing window (111), and outputs electric signals that are related to the motions of the swimmer wearing the swimming goggle. One example of a motion sensor that can be used for this purpose is the LIS332AR motion sensor made by STMicroelectronics. LIS332AR is an accelerometer that measures a three-dimensional acceleration vector, and outputs three voltages, which are proportional to the three components of the acceleration vector along its x, y, and z directions. For the example in FIGS. 5(a-g), the motion sensor (520) can be an LIS332AR accelerometer that is placed at a position where its x axis is pointing towards the viewing direction through the forward viewing window (111), as illustrated by the dashed lined arrows in FIGS. 5(a, b). This direction will be called the "Face direction" in the following discussions. The y axis of the motion sensor (520) is pointing towards the viewing direction through the back stroke viewing window (122), as illustrated by the dashed lined arrows in FIGS. 5(a, b). This direction will be called the "Head direction" in the following discussions. For this example, the electric sound speaker (505) is attached to the head strap (104) of the swimming goggle in FIG. 5(a). The electric sound speaker (505) also can be an earbud or a speaker in other shapes.

Figure 5C:
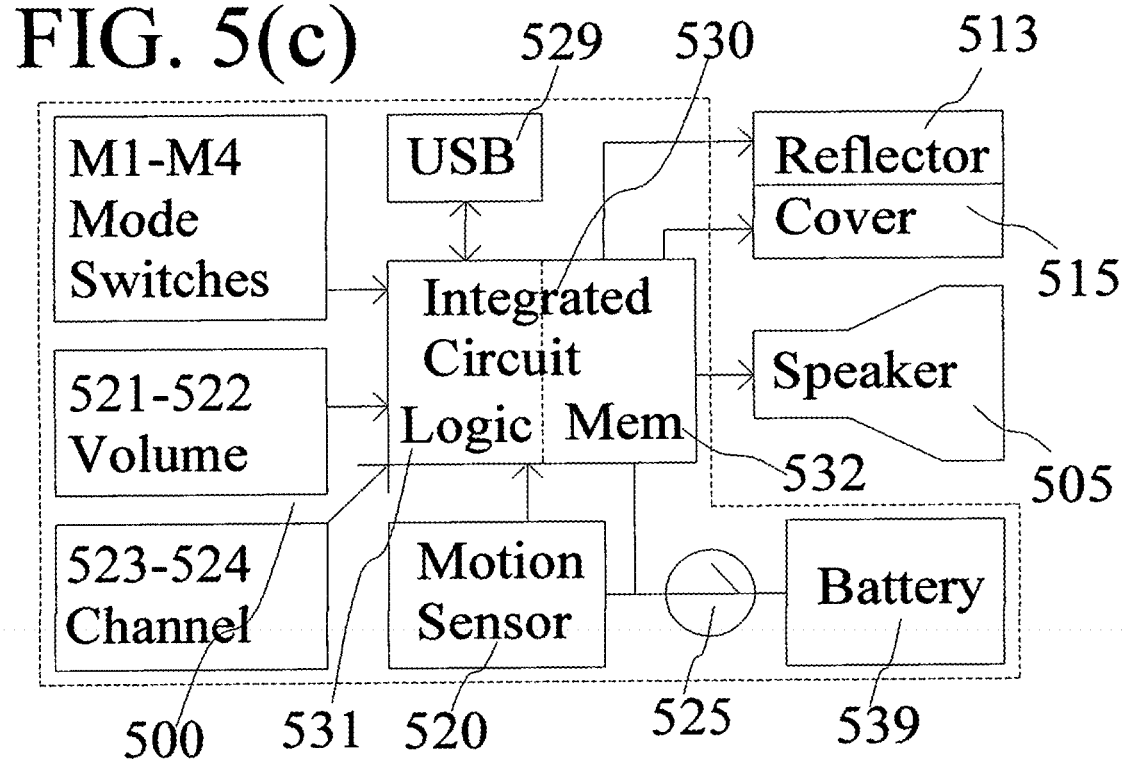
FIG. 5(c) is a symbolic block diagram for the electric controller and output devices in FIG. 5(b)

A user can open the water-tight cover (501) on the swimming goggle to reach the front panel of the electric controller (500). As shown in FIG. 5(b), the front panel of the electric controller (500) comprises a USB interface socket (529), four mode-select switches (M1-M4), two volume control switches (521-522), two channel-select switches (523, 524), and a power switch (525). All the other electric components of the electric controller (500) are sealed in water-proof packages so that they are not visible in FIG. 5(b). The motion sensor (520) is drawn in dashed lines in FIG. 5(b) with dashed lined arrows pointing to the head direction and the face direction. FIG. 5(c) is a block diagram that shows the components of the electric controller (500). The intelligence of the electric controller (500) is provided by an integrated circuit (530). In this example, the integrated circuit (530) comprises a memory module (532) and a logic module (531). One example of the logic module is a programmable microcontroller. One example of the memory module is a FLASH nonvolatile memory device. The memory module (532) and the logic module (531) can be one integrated circuit chip in the same package, and can also be separated integrated circuit chips in separated packages. In this example, the integrated circuit is programmable through the Universal Serial Bus (USB) interface (529) shown in FIGS. 5(b, c). A computer or a mobile electronic device can be used to program the integrated circuit (530) using the USB interface (520). The power lines of the USB interface are connected to a rechargeable battery (539). The electric connection between the rechargeable battery (539) and the integrated circuit (530) is controlled by a power switch (525). This power switch (525) is a toggle switch on the front panel of the electric controller (500), as shown in FIG. 5(b). The mode-select switches (M1-M4) determine the operation mode of the integrated circuit (530); an exemplary list of operation modes is shown in FIG. 5(g). The volume control switches (521, 522) control the volume of the speaker (505). The channel-select switches (523, 524) can be used to select music to be played by the speaker (505).

The logic module (531) of the integrated circuit (530) is able to analyze the outputs of the motion sensor (520) to determine the outputs of the integrated circuit (530), while the swimmer wearing the swimming goggle is swimming in water. The integrated circuit (530) is able to control the position of the reflector (513) and the light blocking cover (515) based on the motions of the swimmer detected by the motion sensor (520). The integrated circuit is also able to control the outputs of the electric sound speaker (505) while the swimmer wearing the swimming goggle is swimming in water.

Figure 5D:
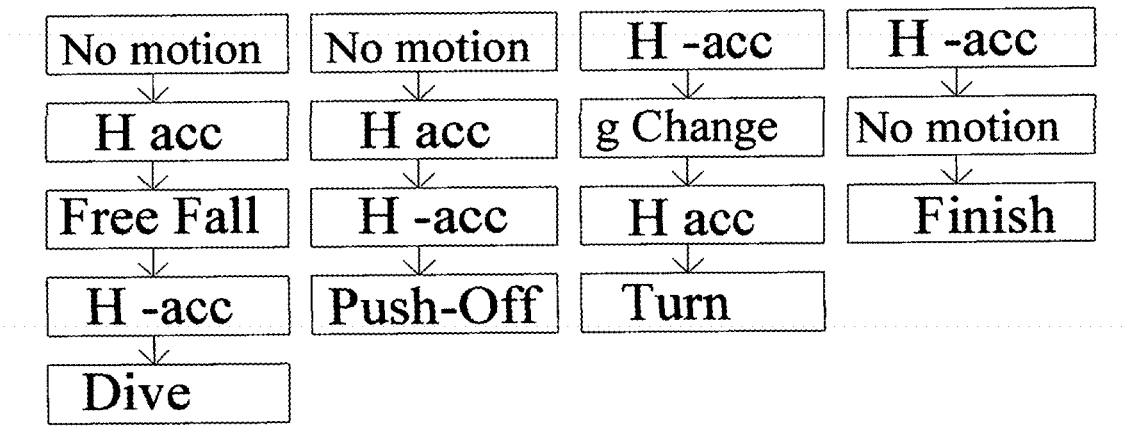
FIG. 5(d) is a symbolic block diagram illustrating how procedures are executed to determine the actions of a swimmer wearing a swimming goggle equipped with the electric controller in FIG. 5(c)
Figure 5D:
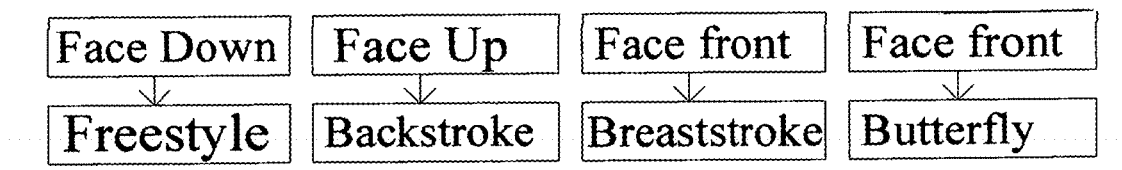

FIG. 5(d) is a simplified symbolic float chart for the sequences of events used to determine the actions of the swimmer using the outputs of the motion sensor (520). In FIGS. 5(d-g), the symbol "H acc" means the motion sensor detected a large acceleration in the head direction, and the symbol "H −acc" means the motion sensor detected a large negative acceleration in the head direction. For example, if the motion sensor (520) detects no motion initially, followed by a large acceleration in head direction (H acc), followed by a free fall, and ending with a large negative acceleration in head direction (H −acc), then the logic module (531) of the integrated circuit (530) would know that the swimmer just dived into water. This process is shown in the first column of FIG. 5(d). If the motion sensor (520) detects no motion initially, followed by a large acceleration in head direction (H acc), and ending with a large negative acceleration in head direction (H −acc) without a free fall in between, then the logic module (531) of the integrated circuit (530) would know that the swimmer just pushed off the wall of a swimming pool. This process is shown in the second column of FIG. 5(d). If the motion sensor (520) detects a large negative acceleration in head direction (H −acc), followed by a change in direction of the gravity g force relative to the orientation of the motion sensor (520), and ending with a large acceleration in head direction (H acc), then the logic module (531) of the integrated circuit (530) would know that the swimmer just performed a flip turn. This process is shown in the third column of FIG. 5(d). If the motion sensor (520) detects a large negative acceleration in head direction (H −acc), which ended with no motion, then the logic module (531) of the integrated circuit (530) would know that the swimmer just finished swimming. This process is shown in the fourth column of FIG. 5(d). The motion sensor (520) also can tell the integrated circuit (530) the angle between gravity acceleration vector (g) relative to the face direction. When the swimming is swimming face down, the integrated circuit (530) would know that the swimmer is swimming freestyle; when the swimming is swimming face up, the integrated circuit (530) would know that the swimmer is swimming backstroke; and when the swimming is swimming face front for a period of time during each stroke, the integrated circuit (530) would know that the swimmer is swimming either breaststroke or butterfly, which can be distinguished by detailed analysis, as shown by the examples in FIG. 5(d).

Figure 5E:
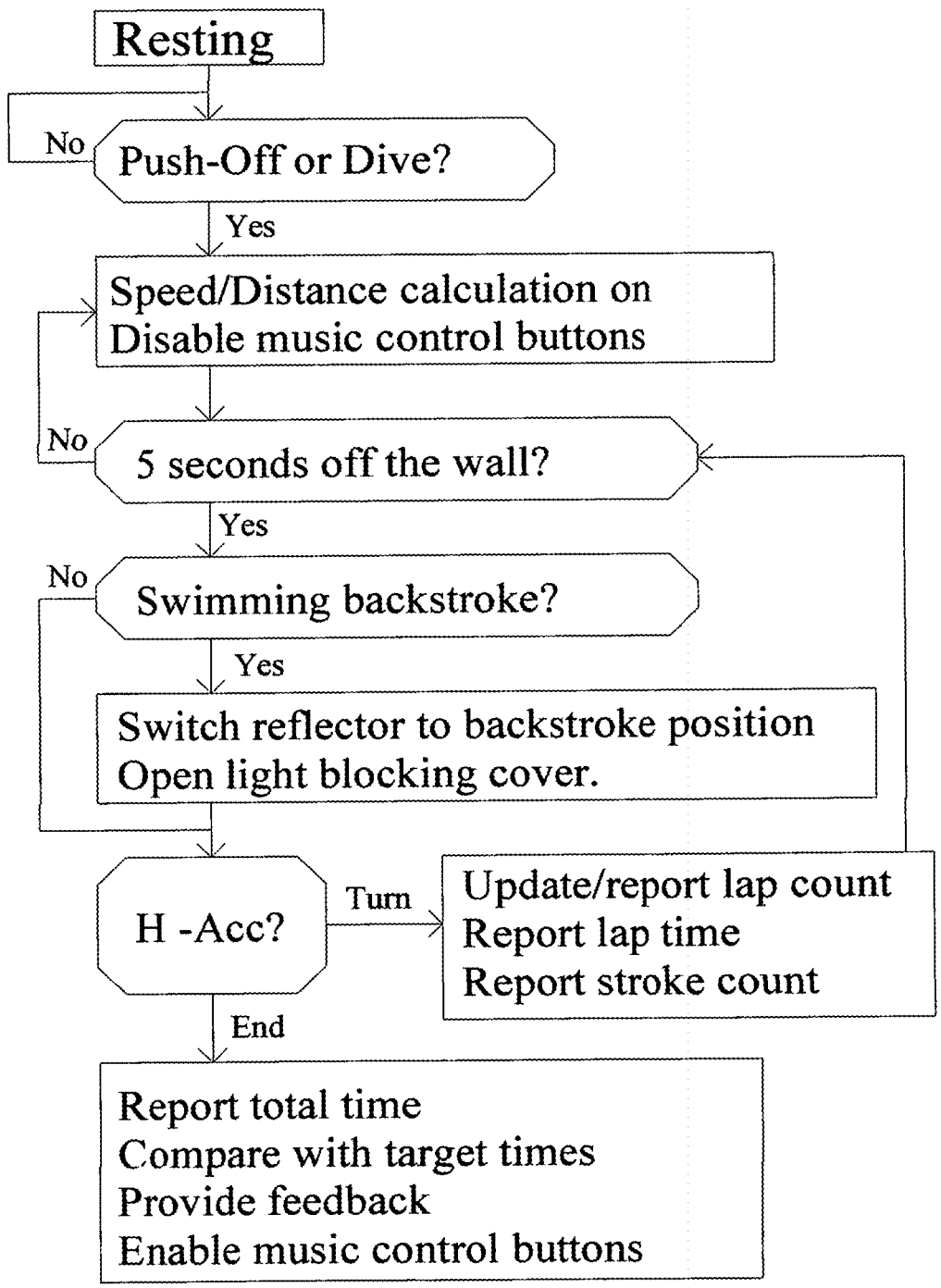
FIG. 5(e) is a flowchart for an exemplary application program used by the electric controller in FIG. 5(c)

Using the procedures in FIG. 5(d) to determine the actions of the swimmer, application programs stored in the non-volatile memory (532) of the integrated circuit (530) in the electric controller (500) can support sophisticated control of the light reflector (513), the light blocking cover (515), and the electric sound speaker (505). FIG. 5(e) is a flowchart for an exemplary application program used by the electric controller in FIG. 5(c). When a dive or push-off is detected after a resting state, the integrated circuit (530) starts to execute speed and distance calculations. If the motion sensor (520) is an accelerometer, speed can be calculated by integration of acceleration along head direction, and distance can be calculated by integration of speed. Using the electric sound speaker (505), the integrated circuit (530) also can play music that is stored in integrated circuit memory device (532). The volume and channel control buttons (521-524) also can be disabled to prevent accidental changes caused by water, which can exert forces against the buttons. Furthermore, the integrated circuit (530) would measure time using an internal timer, wait for 5 seconds, and check if the swimmer is swimming in backstroke or not by detecting face direction of the swimmer. If the swimmer is swimming backstroke, the integrated circuit (530) switches the light reflector (513) to backstroke position, and opens the light blocking cover (515) so that the swimmer can view the end of the swimming pool. The integrated circuit can also lap count. After the motion sensor (520) detects a large negative acceleration in the head direction (H −Acc), the integrated circuit (530) analyzes the next action of the swimmer. If the swimmer makes a turn, then the integrated circuit (530) updates the lap count, and reports the lap count to the swimmer using the electric sound speaker (505); optionally, the lap time and stroke count of the swimmer also can be reported to the swimmer at this time. If the swimmer stops swimming, then the integrated circuit (530) reports the total time to the swimmer using the electric sound speaker (505); optionally, the total time can be compared with target times, and the integrated circuit (530) can provide feedback such as encouraging words using the electric sound speaker (505); music also can be turned off, while the volume and channel control buttons (521-524) can be enabled at this time.

Figure 5F:
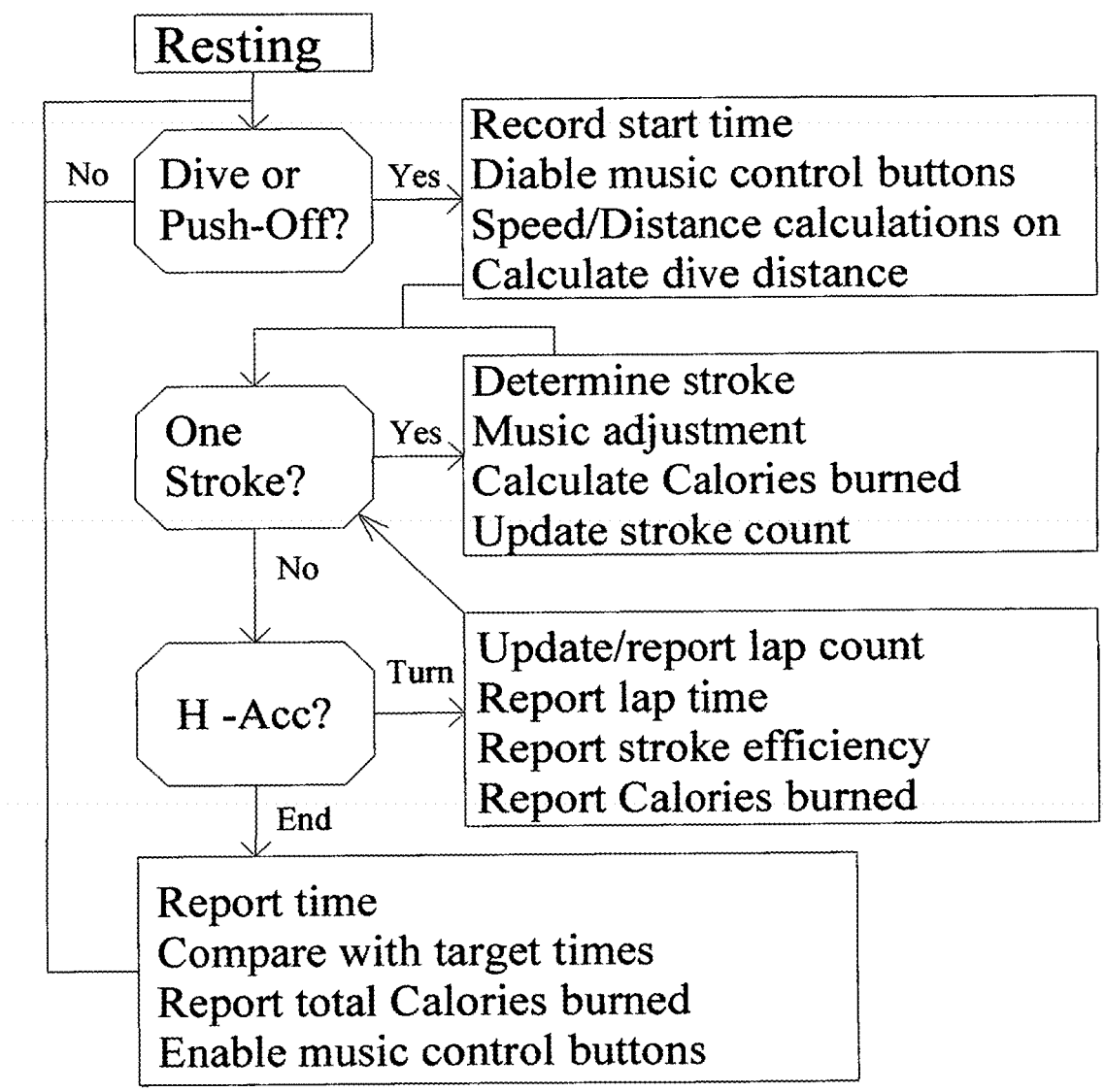
FIG. 5(f) is a flowchart for another exemplary application program used by the electric controller in FIG. 5(c)

FIG. 5(f) is a flowchart for another exemplary application program used by the electric controller in FIG. 5(c). In this example, when a push-off or a dive is detected after resting state, the integrated circuit (530) starts time measurement, disables volume and channel control buttons (521-524), and starts speed and distance calculations. It also can measure dive distance. After the swimmer takes a stroke, the integrated circuit (530) determines the stroke type and updates the stroke count. The integrated circuit (530) can also estimate the number of Calories burned by the swimmer based on the outputs of the motion sensor. Feedback can be provided using voice through the electric sound speaker (505). After the motion sensor (520) detects a large negative acceleration in the head direction (H −Acc), the integrated circuit (530) analyzes the next action of the swimmer. If the swimmer makes a turn, then the integrated circuit (530) will update the lap count, and report the lap count to the swimmer using the electric sound speaker (505); optionally, the lap time, stroke count, and Calories burned by the swimmer also can be reported at this time. If the swimmer stops swimming, then the integrated circuit (530) reports the total time to the swimmer using the electric sound speaker (505); optionally, the total time can be compared with target times, and the integrated circuit (530) can provide feedback such as encouraging words using the electric sound speaker (505). The total number of Calories burned by the swimmer can be reported, while the volume and channel control buttons (521-524) can be enabled at this time.

While the preferred embodiments have been illustrated and described herein, other modifications and changes will be evident to those skilled in the art. It is to be understood that there are many other possible modifications and implementations so that the scope of the invention is not limited by the specific embodiments discussed herein. Using a programmable integrated circuit, a swimming goggle equipped with an electric controller is capable of performing wide varieties of functions to support a swimmer wearing the swimming goggle. FIG. 5(g) shows a table that lists exemplary modes supported by the electric controller in FIG. 5(c). For example, when the mode-select switches (M1-M4) are set to be (0, 1, 0, 0), the electric sound speaker (505) is enabled to play music. The electric sound speaker (505) is able to change the way to play music depending on the motions of the swimmer wearing the swimming goggle. For example, when the mode-select switches (M1-M4) are set to be (0,1,1,0), the electric sound speaker (505) plays music with a pace that is synchronized with the swimming pace of the swimmer; when the mode-select switches (M1-M4) are set to be (0,1,1,1), the integrated circuit (630) adjusts the volume of the music played by the electric sound speaker (505) according to the swimming speed of the swimmer; when the mode-select switches (M1-M4) are set to be (1,0,1,1), the integrated circuit (630) uses the electric sound speaker (505) to provide a voice report of the estimated number of Calories burned by the swimmer; and when the mode-select switches (M1-M4) are set to be (1,1,1,1), the integrated circuit (630) store data to the non-volatile memory for further detailed analysis. The electric sound speaker of the swimming goggle is able to play music at a beat or a volume that is related to the motions of the swimmer wearing the swimming goggle. More examples are listed in FIG. 5(g).

The exemplary electronic controller (500) and the electric sound speaker (505) in FIG. 5(a) are embedded inside a swimming goggle. When the electronic controller is built-in as part of a swimming goggle, it is naturally inseparable from the goggle, which allows the controller to withstand forces exerted by the water while swimming. The disadvantage of having an embedded electric controller in a swimming goggle is that the controller will be useless once the goggle breaks or wears out. FIGS. 6(a-c) are simplified symbolic diagrams showing the structures of an exemplary electronic attachment for a swimming goggle that solves the problem. The electronic device (600) in this example is able to withstand strong forces in the water when swimmers are diving, turning, or swimming various strokes at high speeds. Furthermore, this electronic device (600) can be detached from the swimming goggle (650) so that the same electronic device can be used with different swimming goggles.

FIG. 6(a) is a simplified symbolic diagram showing a swimmer wearing a swimming goggle (650) with an electronic device (600) attached to the head strap (104) of the swimming goggle. For this example, the swimming goggle comprises an eye socket that has a transparent forward viewing window attached to a goggle frame, where the goggle frame has a backstroke viewing window opened on a top portion of the goggle frame disposed away from the transparent forward viewing window, and a position-switchable light blocking cover (515) attached to an edge of the backstroke viewing window. This light blocking cover (515) can switch position with respect to the edge of the backstroke viewing window. Its position is controlled electronically by the electronic device (600) that is attached to the swimming goggle. This swimming goggle (650) further comprises a position-switchable light reflector (513) that can switch positions with respect to the front viewing window of the eye socket. The position of the position-switchable light reflector (513) is controlled electronically by the electronic device (600) attached to the swimming goggle.

The electronic device (600) attached to the head strap (104) of the swimming goggle (650) comprises a motion sensor (620), an electric sound speaker (605), an integrated circuit (630), a water-proof package (609) that encloses the motion sensor (650) and the integrated circuit (630), and a connector to attach the water-proof package (609) to the head strap (104) of a swimming goggle (650). In this example, a loop Velcro (641) and a hook Velcro (642) wrap around the head strap (104) of the swimming goggle (650) to provide a reliable attachment between the water-proof package (609) and the head strap (104) of the swimming goggle (650), as shown in FIGS. 6(a-c). The water-proof package (609) also can enclose other components such as a USB interface socket, none-volatile memory device (632), battery, power switches, and other control switches. As shown in FIG. 6(b), the front panel of the water-proof package (609) comprises two volume control switches (621-622), two channel-select switches (623, 624), and a power switch (625); it can also have a USB interface socket and mode-select switches placed at the back side of the package. A motion sensor (620) is placed inside the electronic device (600) as shown by the dashed lines in FIG. 6(a). While in use, this motion sensor (620) is attached near the ear of the swimmer, where its x axis is pointing towards the "face direction", and its y axis is pointing towards the "head direction", as illustrated by the dashed lined arrows in FIG. 6(a). The integrated circuit (630) in the electronic device (600) is able to read the outputs of the motion sensor (620) and analyze the motions of the swimmer wearing the swimming goggles with the attached electronic device while the swimmer is swimming in water. The electronic device (600) illustrated in FIGS. 6(a-c) comprises all the components of the electronic controller (500) described in FIGS. 5(a-c). Therefore, it is able to support all the functions described in FIGS. 5(d-g).

For the example in FIGS. 6(a-c), the electrical sound speaker (605) is placed inside an earbud. Typical earbuds would easily fall out while the swimmer is swimming in water. The electrical sound speaker (605) in this example is placed inside an earbud that has a moldable ear tip (606), as shown in FIGS. 6(a-c). This moldable ear tip (606) can be molded into different shapes in order to tightly fit the external ear canal of different users. In addition, the earbud (605) is connected to the water-proof package (609) of the electronic device with a solid elastic connector (607). This elastic connector (607) provides an elastic force that helps push the earbud into the external ear canal of the swimmer, as illustrated in FIGS. 6(a-c). As a result, the earbud (605) will not fall out when the swimmer is diving, turning, or swimming at high speed.

Figure 5H:
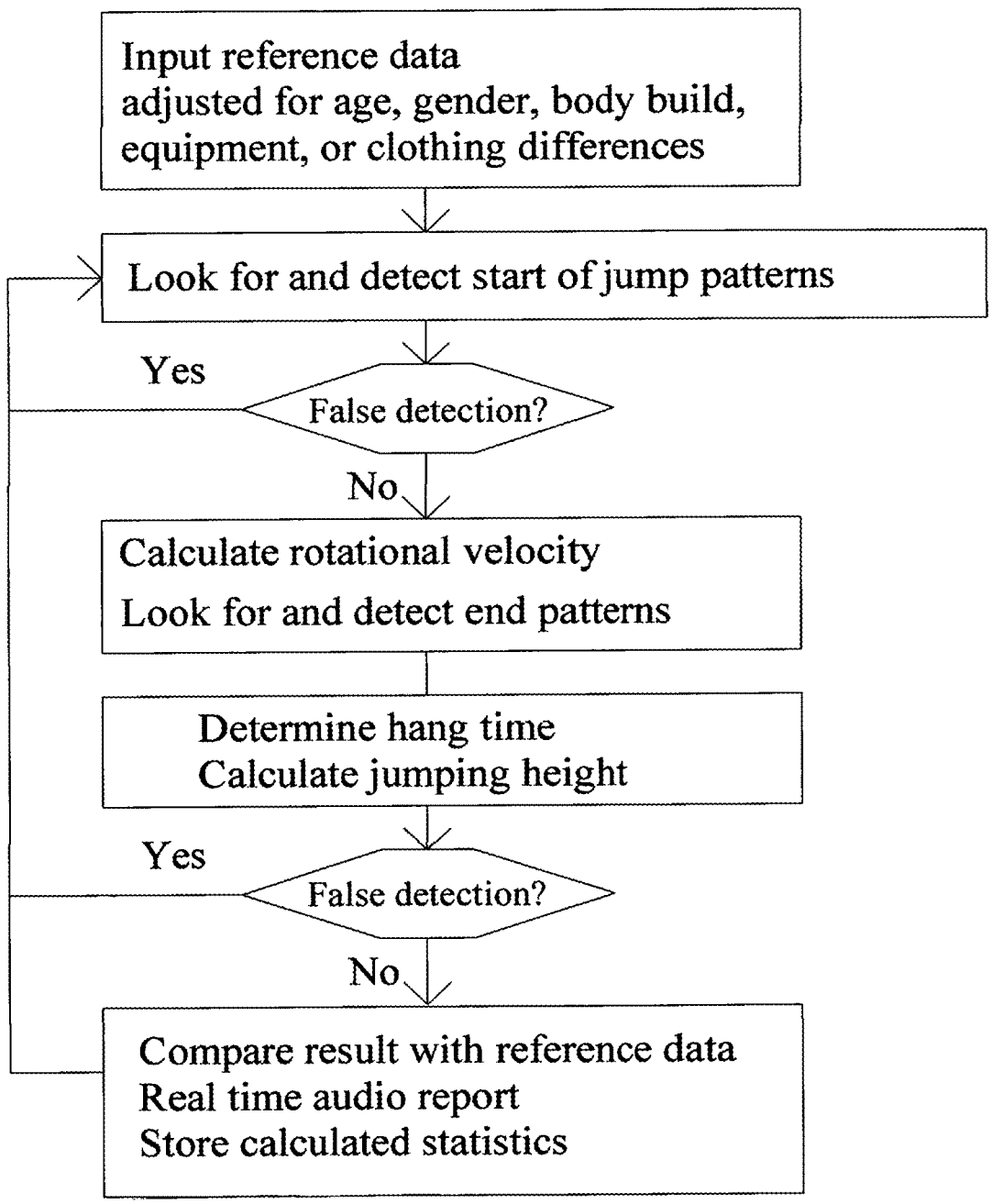
FIG. 5(h) is an exemplary flowchart for the logic behind the jumping analysis functions of the wearable electronic device of the present invention.
Figure 5I:
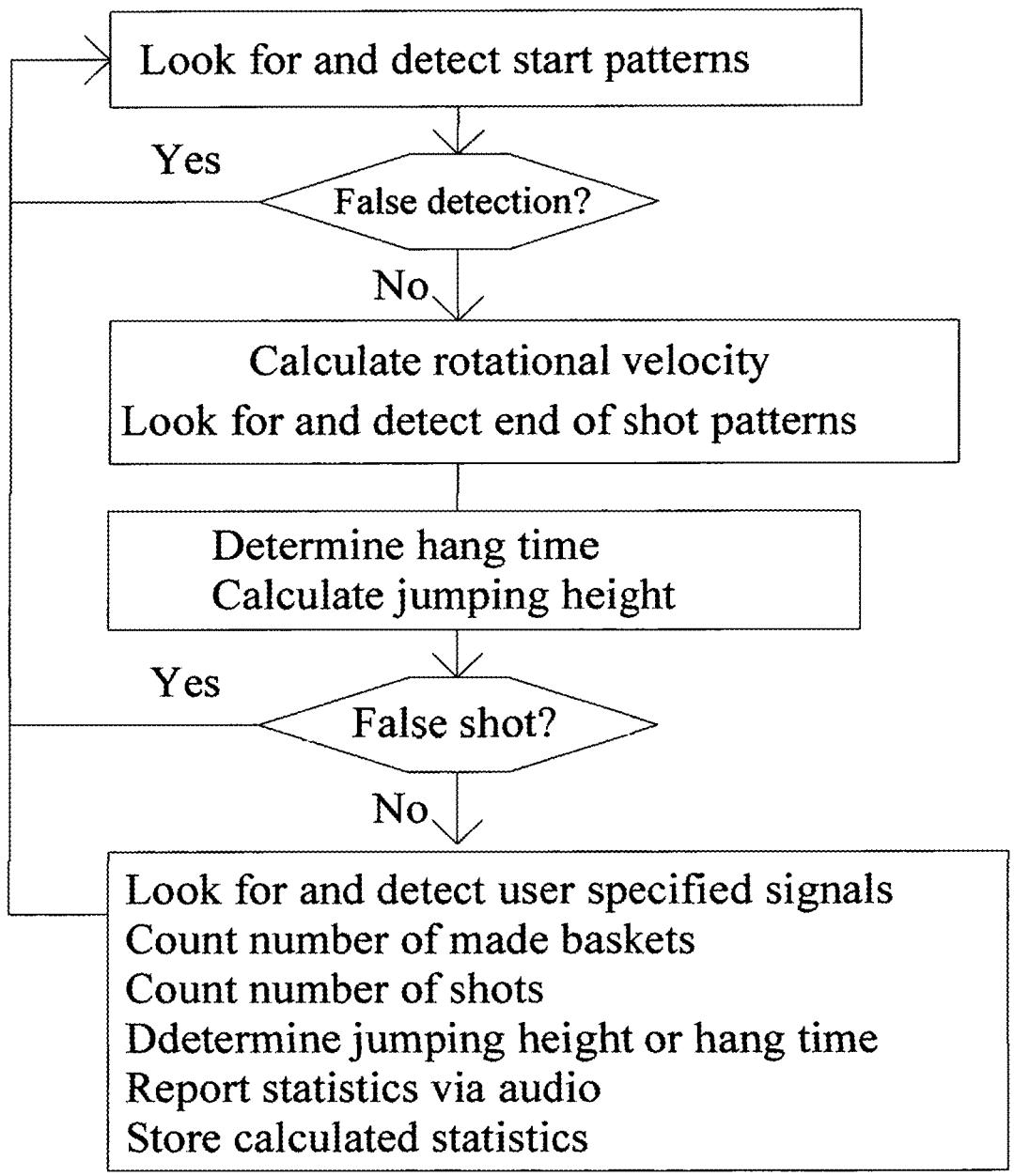
FIG. 5(i) is an exemplary flowchart for the logic behind the basketball performance analysis functions of the wearable electronic device of the present invention.
Figure 5J:
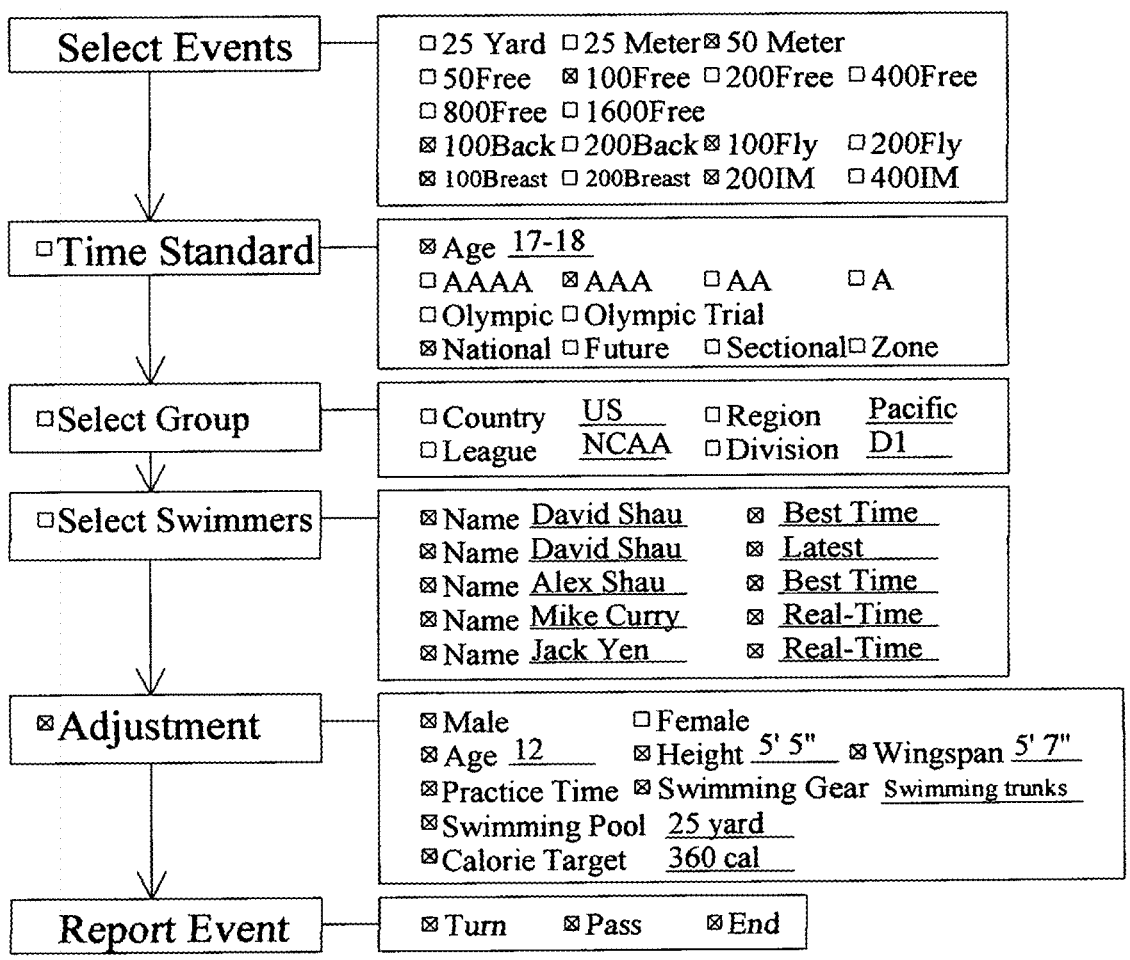
FIG. 5(j) is an exemplary flowchart for various methods for selecting reference swimming data.

FIG. 5(j) is an exemplary flowchart for various methods for filtering and selecting reference data from a large database. For example, a user can select the swimming events for the comparisons such as the 100-meter freestyle, 100-meter backstroke, 100-meter butterfly, 100-meter breaststroke, and 200-meter individual medley, as shown in FIG. 5(j). A user can also select widely accepted swimming time standards as a reference. Swimming time standards are standardized times for certain swimming events that are widely accepted. For example, in 2016, the Olympic Trials swimming time standard for the men's 100-meter freestyle was 50.69 seconds. It was internationally recognized and accepted that male swimmers who achieved that time standard could compete in the 100-meter freestyle at their respective country's 2016 Olympic Trials. In FIG. 5(j), the user selected the 17-18 age group AAA time standard and the Nationals time standard as reference times. By choosing these swimming events and swimming time standards, the user will be able to swim those events, and receive audio feedback from the electrical sound speaker (705) that can state how close the user is to the selected time standards after the user finishes swimming that event. In addition, the user can receive audio feedback from the electrical sound speaker (705) that indicates how many seconds ahead or behind pace the user is from a selected time standard while the user is swimming the event that corresponds to that time standard. A user can also indicate what population of swimmers he or she would like to be compared to. For example, the user selected to compare his or her swimming performance to swimming times recorded by NCAA division 1 swimmers in the pacific region of United States, as shown in FIG. 5(j). The reference swimming data stored in the wearable electronic device can also represent a specific swimming time of a selected swimmer or a previous swimming time of the user wearing the wearable electronic device. Therefore, a user can indirectly compete with one or many individual swimmers. For example, the user selected to compare his or her swimming time to David Shau's recorded fastest swimming time, David Shau's recorded latest swimming time, and Alex Shau's recorded fastest swimming time. In addition, the user also selected to compete with Mike Curry and Jack Yen in real time, as shown by the example in FIG. 5(j). Using wearable electronic devices (940) equipped with wireless interfaces, it is possible to compare the swimming performance of multiple swimmers while they are all swimming in water, even when they are separated by long distances.

Sometimes it is not practical trying to compete with swimmers who possess unfair advantages over the user. For example, a 12-year-old younger brother would not likely be able to achieve similar swimming times of his 25-year-old brother. However, a wearable electronic device of the present invention can use the swimming data of the 25-year-old brother and account for age difference to generate a set of reference data that represents the relative performance of the older brother at 12 years old. In this way, the younger brother can use a wearable electronic device of the present invention to compete with his older brother on a relative scale instead of a literal scale—as if his older brother were actually 12 years old. Similarly, the reference data can be adjusted for differences in body types. For example, a younger brother who is 5 feet 5 inches tall can fairly compete with a 6 foot 4-inch-tall older brother using scaled and adjusted reference data calculated from the swimming results of said older brother. The reference data of the 6 foot 4-inch-tall brother would be adjusted and scaled to a dataset that represents the older brother as if he were 5 feet 5 inches tall. Similar adjustments are applicable to differences in wingspan, shoe size, hand size, or other body type differences. Furthermore, this method of relative scaling can also be applied to differences in swimming experiences, or total number of hours spent swimming. For example, a recreational swimmer can compete with a competitive or professional swimming on a similar relative scale as mentioned before. Furthermore, the differences in swimming gear can also be accounted for. For example, reference data recorded by a swimmer wearing a technical suit can be scaled to an equivalent dataset of the same swimmer wearing swim trunks, as shown in the examples in FIG. 5(j). The user can also customize when he or she will receive notifications from the wearable electronic device (940) regarding comparison results. For example, the wearable electronic device (940) can notify the user the time differences relative to swimming times in the reference data after each lap or at the end of a swimming event. The wearable electronic device (940) also can notify the user when the user has passed a swimmer, or in other words covered more distance in the same amount of time, represented by a set of reference data. Similar comparison functions are also applicable to other physical activities such as running, biking, climbing, walking, jumping, and so on.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, the wearable device in FIGS. 6(a-c) and other wearable devices of the present invention can also analyze jumping actions performed by the user.

Figure 7A:
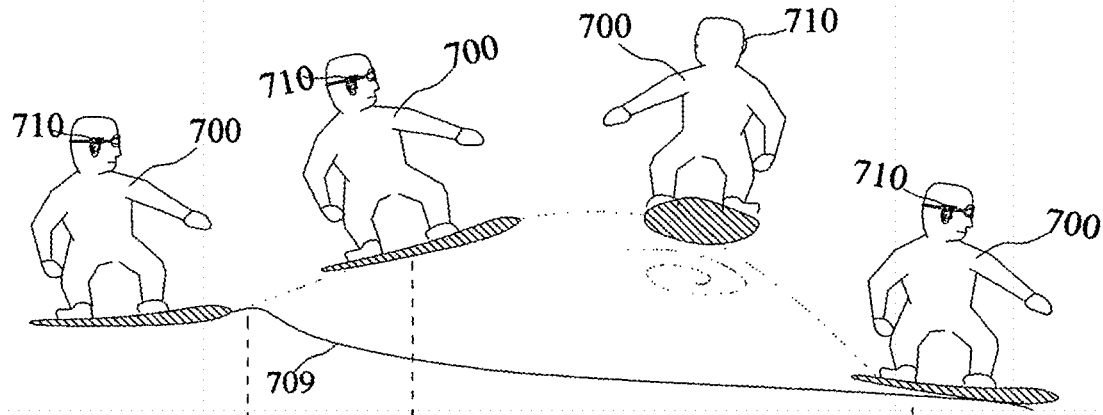
FIG. 7(a) is a simplified exemplary diagram displaying the time progression of a snowboarder (700) going airborne while snowboarding.
Figure 7B:
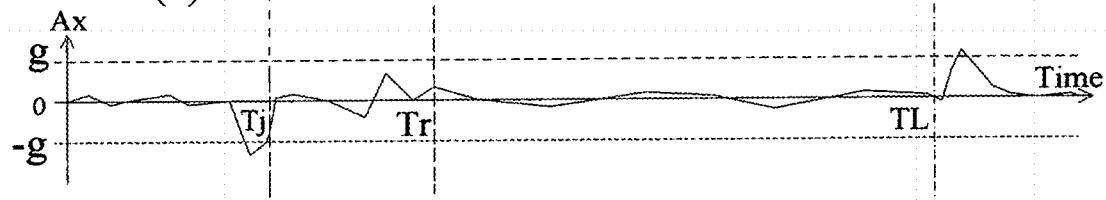
FIGS. 7(b-e) show exemplary waveforms of the acceleration vector components (Ax, Ay, Az, and Ap respectively) detected by the motion sensor in the wearable electronic device (710) worn by the snowboarder in FIG. 7(a)
FIG. 7(f) shows a close view of the wearable electronic device (710) worn by the snowboarder in FIG. 7(a)
Figure 7C:
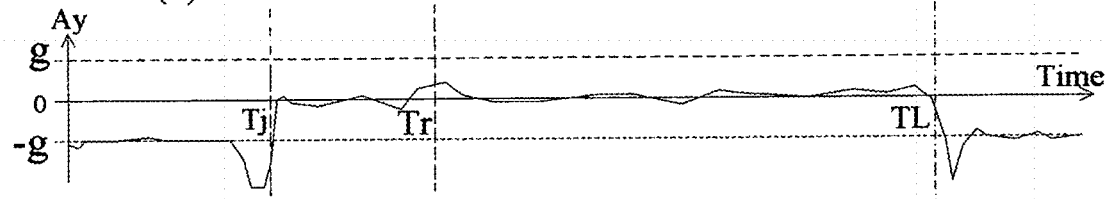
Figure 7D:
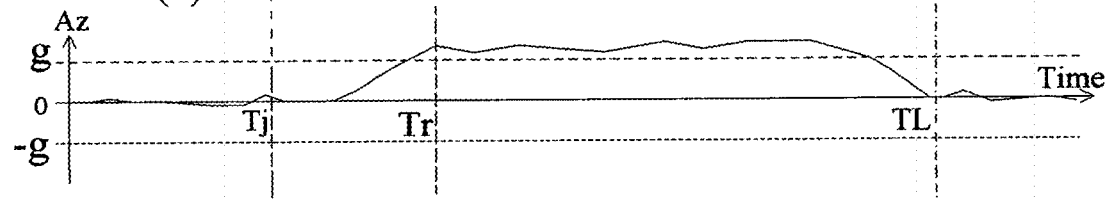
Figure 7E:
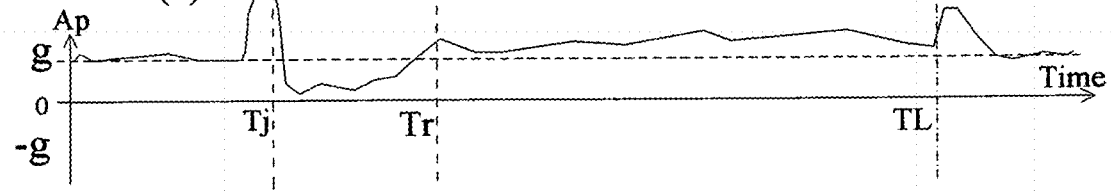
Figure 7F:
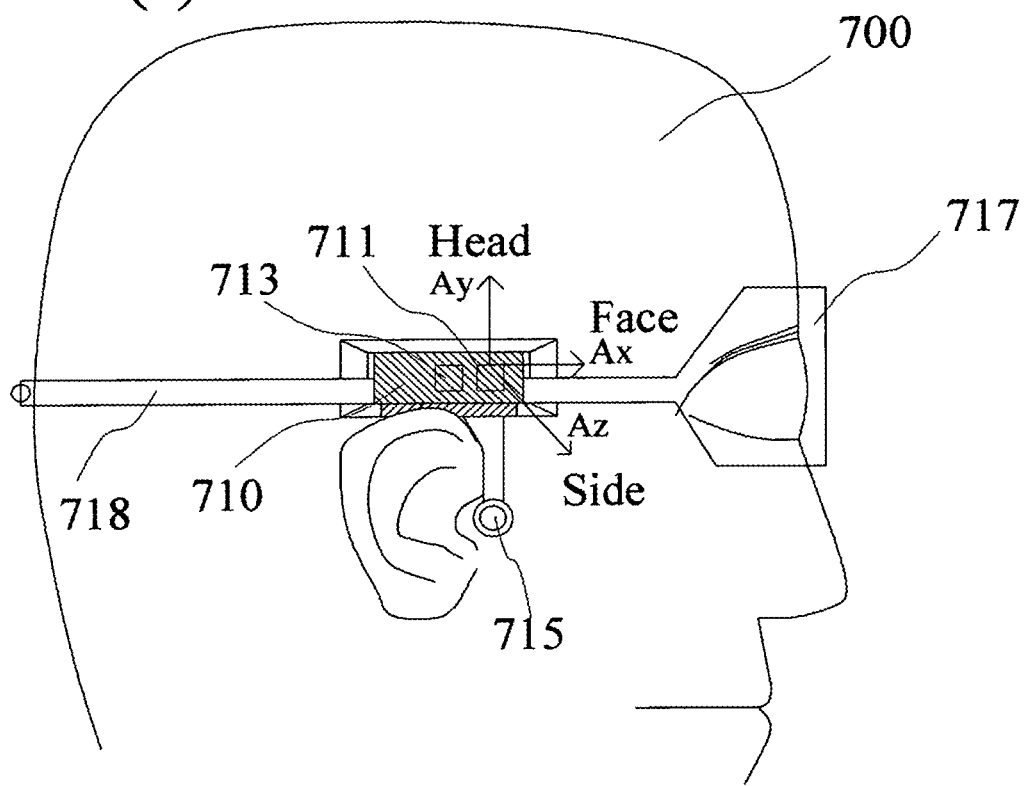

FIG. 7(a) shows a time progression of a snowboarder (700) wearing a wearable electronic device (710) of the present invention as he/she transitions from snowboarding on snow, to spinning in the air, to landing on the snow once again. FIG. 7(f) displays a closer view of the wearable electronic device (710) worn by the snowboarder (700) in FIG. 7(a). This device (710) has the same structure as the wearable electronic device (610) in FIGS. 6(a-c), with the exception that it is now attached to the head strap (718) of a pair of snowboarding goggles (717) as shown in FIG. 7(f), as opposed to a head strap of a pair of swimming goggles. This wearable electronic device (710) also comprises a motion sensor (711), an integrated circuit (713) that uses the outputs of the motion sensor to determine the hang time, jump height, or other athletic statistics pertaining to the user when the user is airborne, and an electrical sound speaker (715). In this example, the motion sensor (711) is an accelerometer. The x-component (Ax), y-component (Ay), and z-component (Az) of the acceleration vectors measured by the motion sensor (711) are all represented by the triaxial arrows in FIG. 7(f). In this example, the x-axis of the motion sensor (711) is pointing toward the user's forward viewing direction, as shown by the arrow (Ax) in FIG. 7(f). In previous sections, this direction was also referred to as the "face direction" of swimmers; a similar meaning will be adopted for the following examples. More specifically, this face direction points away from the user's body, where a unit vector along the face direction would be approximately normal to the surface of the user's forehead. The y-measurement axis of the motion sensor (711) is pointing towards the top of the head of the user, as illustrated by the arrow (Ay) in FIG. 7(f). In previous sections, this direction was referred to as the "head direction" of swimmers; a similar meaning will be adopted for the following examples. More specifically, this head direction points away from the user's body, where a unit vector along the head direction would be approximately normal to the top of the user's head. The z-measurement axis of the motion sensor (711) is pointing in the direction perpendicular to the user's temple, as illustrated by the arrow (Az) in FIG. 7(f). This direction will now be referred to as the "side direction" in the following discussions. More specifically, this side direction points towards the right or left of the head of the user, such that a unit vector along the side direction would be approximately normal to the user's temple. The amplitude (Ap) of the acceleration vector is defined to be the square root of (Ax*Ax+Ay*Ay+Az*Az).

FIGS. 7(b-e) show exemplary waveforms of the acceleration vector components detected by the motion sensor (711) of the wearable electronic device (710): Ax, Ay, Az, and Ap. Initially, the snowboarder (700) travels at a constant speed. This results in measurements of Ax and Az that are approximately zero, and measurements of Ay that are approximately −g, where g is the amplitude of the gravity acceleration vector, as shown in FIGS. 7(b-d). As a result, Ap is approximately g, as shown in FIG. 7(e). Moments before the snowboarder goes aerial at time Tj, the snowboarder's speed increases, as reflected by the waveforms of Ax, Ay, and Ap in FIGS. 7(b), 7(c), and 7(e) respectively. After the snowboarder goes airborne at time Tj, the snowboarder (700) remains in the air such that the amplitudes of Ax and Ay approach zero immediately after time Tj. In this example, the snowboarder (700) executes clockwise rotations between time Tr and TL, as illustrated in FIG. 7(a), such that the motion sensor (711) in the electronic wearable device (710) detects positive accelerations in the side direction (Az) during this interval. These accelerations in the side direction stay significantly greater than zero until near the landing time TL, when the snowboarder slows down his rotational speed, as illustrated in FIG. 7(d). At the time of landing (TL), the wearable electronic device (710) detects significant decelerations along the face direction (Ax) and accelerations in the direction opposite to that of the head direction (Ay). The accelerations in the side direction (Az) return to approximately zero now that the snowboarder has ceased to rotate. All the mentioned changes in accelerations near the time of landing (TL) are shown in FIGS. 7(b-d). As illustrated by this example, the amplitude of the acceleration vector (Ap) is typically non-zero unless the snowboarder refrains from performing any actions or physical movements while airborne. Therefore, Alexander's methods disclosed in U.S. Pat. No. 8,108,177 are not applicable to practical jumping actions that have varying acceleration patterns in the air.

FIG. 5(h) is an exemplary flowchart for the logic behind the jumping analysis functions of the wearable electronic device of the present invention that is able to analyze realistic and various jumping actions such as those illustrated in FIGS. 7(a-e). The reference data can either represent jumping performances of a different user or previous jumping performances of the same user and can be stored in the wearable electronic device (710). Examples of jumping performances can include the number of jumps executed, jump height achieved, hang time achieved, rate of rotation, and other statistics related to various types of jumps and leaps. Similar to previous examples for swimming, these reference data can be adjusted for differences in age, gender, height, body build, equipment, or clothing worn. The integrated circuit (713) analyzes the outputs of the motion sensor (711) in the wearable electronic device in order to detect specific patterns that indicate the beginning of a jump. For example, sudden accelerations in the face (Ax) and head (Ay) directions subsequently followed by near zero values of Ax and Ay typically reflect movement patterns of the beginning of a jump, as shown by the example in FIGS. 7(a-e) moments before the jump at time Tj. The integrated circuit (713) continuously looks for patterns that indicate the beginning of a jump, and once the beginning of a jump is detected, timing modules in the integrated circuit begin to measure the user's time of flight. Although the beginning of a jump could be falsely detected, the firmware and the logic modules in the integrated circuit (711) comprise algorithms to account for such false detections. If a false detection is caught by the algorithms, the integrated circuit discards the detection, and returns to looking for patterns that could indicate the beginning of a jump, as shown by the flow chart in FIG. 5(h). An example of an acceleration pattern that could indicate a false detection is when similar non-zero acceleration values in the Ax or Ay direction is continuously detected after the beginning of a jump is detected. If the detection is not a false detection, then the wearable electronic device (710) will subsequently analyze motion signals and perform calculations that yield jumping statistics such as the rotational velocity or rate of rotations of the user, while simultaneously looking for patterns that indicate the end of a jump. For example, sudden decelerations or very positive or negative peaks in the face direction (Ax) waveform and/or very negative or positive peaks in the head direction (Ay) waveform can indicate the end of a jump, as illustrated by the example in FIGS. 7(a-e), when the snowboarder lands at time TL. Once the end of a jump is detected, the wearable electronic device (710) determines the hang time and calculates the height of the jump. At this point, the algorithms can still check to see if the jump was a false detection. For example, extremely short hang times of less than 0.25 seconds indicate a high likelihood of a false detection, while hangtimes that are extremely long could indicate a high likelihood of a false detection as well. If the jump was confirmed to be a true jump and not a false detection, then the wearable electronic device can subsequently compare current jumping performances of the user wearing the wearable electronic device to the jumping performances stored in the reference data, and then report the comparison result using the electrical sound speaker (715) to the user in real time. Other parameters such as vertical jump height, number of full rotations executed, rotational velocity, and hang time can also be reported to the user (700) from the electrical sound speaker (715) in real time. Data can also be stored into memory devices in the wearable electronic device (710) as records for future analysis. Wearable electronic devices of the present invention provide objective comparisons between the effects of different equipment on the user's jumping performance. Such equipment includes but is not limited to various shoes, skis, snowboards, ice skates, roller skates, and rollerblades. Notice also how the jumping logic does not make any assumptions for the acceleration patterns of the user while the user is airborne, when determining hang time; the logic only considers the continuous length of time from the point in time at which the beginning of a jump was detected to the point in time at which the end of the jump was detected. These algorithms are therefore able to analyze practical jumping actions that prior art methods cannot.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, in addition to snowboarding, the wearable device in FIGS. 6(a-c) and other wearable devices of the present invention also can analyze jumping actions that are typically executed in other sports such as basketball, volleyball, skiing, skateboarding, roller blading, roller skating, figure skating, stunt biking, diving, gymnastics, high jump, long jump, triple jump, or pole vault.

Figure 8A:
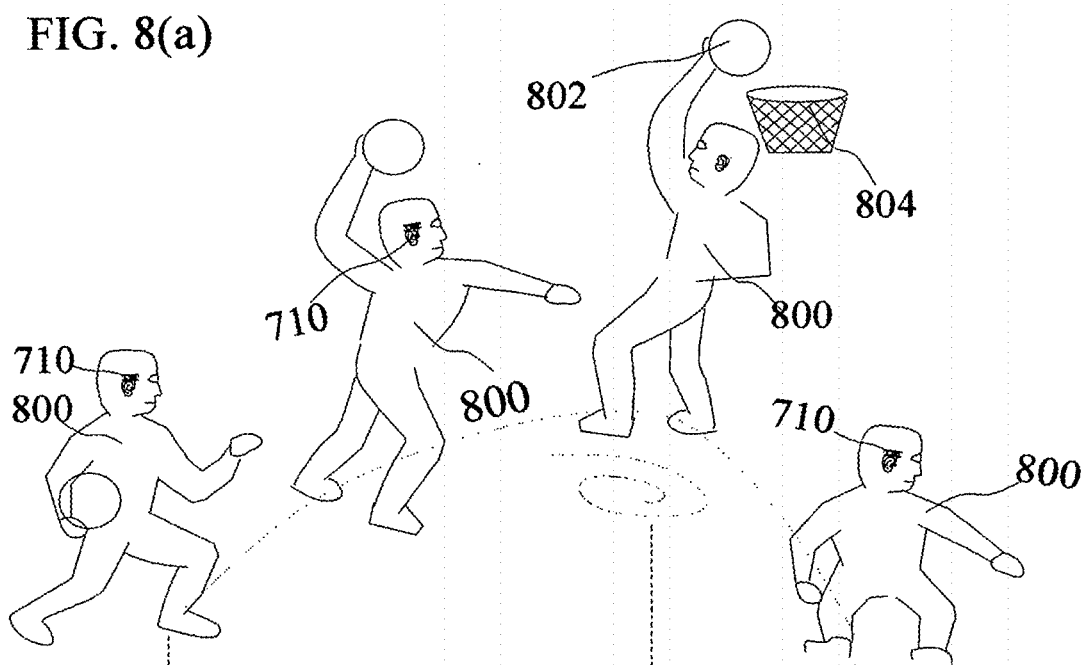
FIG. 8(a) is a simplified exemplary diagram showing the time progression of a basketball player (800) who attempts to make a spinning dunk.
Figure 8B:
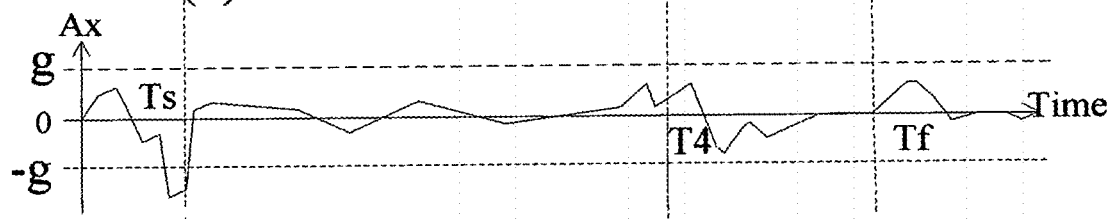
FIGS. 8(b-d) show exemplary waveforms of the acceleration vector components (Ax, Ay, and Az respectively) detected by the motion sensor in the wearable electronic device (710) worn by the basketball player in FIG. 8(a).
Figure 8C:
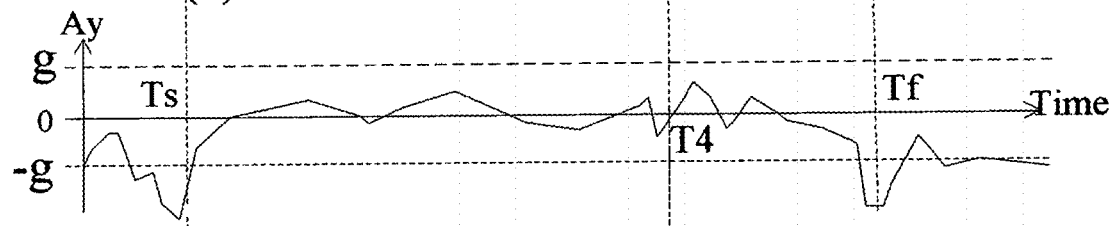
Figure 8D:
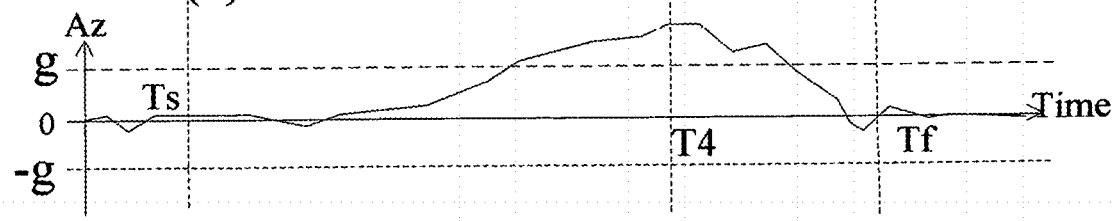

FIG. 8(a) shows a basketball player (800) performing a dunk while rotating in the air while wearing a wearable electronic device (710) of the present invention. The wearable electronic device (710) has the same structure as the one in the snowboarding example, with the exception of it being attached to the ear of the user (800) without the need of a head strap. For example, this can be done using an ear hook that securely hooks the device onto the ear of the user, preventing the device (710) from falling out or off. FIGS. 8(b-d) show exemplary waveforms of the acceleration vector components (Ax, Ay, Az) detected by the motion sensor in the wearable electronic device (710) worn by the basketball player (800) in FIG. 8(a). In this example, before the time at which the player jumps (Ts), the player (800) is dribbling the ball while running. During this period of time, the x and y accelerations (Ax, Ay) bounce up and down, resulting in a pointy, sinusoidal-like waveform, while the z-component (Az) remains close to zero. This pattern is similar to the acceleration waveforms that would result from running, as shown in FIGS. 8(b-d). When approaching the time of takeoff (Ts), the basketball player (800) takes two steps and increases his/her speed, as shown by the waveforms of Ax and Ay in FIGS. 8(b, c). At time Ts, the basketball player (800) jumps into the air, subsequently causing the amplitudes of Ax and Ay to approach zero for a period of time. In this example, the basketball player (800) executes rotations in the air and dunks the ball (802) into the basket (804), as illustrated in FIG. 8(a). As a result, the motion sensor (711) in the electronic wearable device (710) detects large accelerations in the side direction (Az) before and after the player (800) dunks the ball at time (T4), as illustrated in FIG. 8(d). At the time of landing (Tf), the wearable electronic device (710) detects large decelerations along the face direction (Ax), large accelerations opposite to the head direction (Ay), and accelerations in the side direction (Az) that decrease in magnitude until they reach approximately zero, as shown in FIGS. 8(b-d). As illustrated by this example, the amplitude of the acceleration vector (Ap) is non-zero unless the user executes a simple jump without performing any additional actions in the air. Therefore, Alexander's methods disclosed in U.S. Pat. No. 8,108,177 are not applicable to such jumping conditions.

FIG. 5(i) is an exemplary flowchart for the logic behind the jumping analysis functions of the wearable electronic device of the present invention that analyzes possible jumping actions such as those illustrated in FIGS. 8(a-d). The integrated circuit (713) analyzes the outputs of the motion sensor (711) in the wearable electronic device to detect specific patterns that indicate the beginnings of a basketball shot. Jump shots, for example, typically begin similarly to standing vertical jumps. In contrast, layups typically begin with acceleration patterns similar to acceleration patterns seen in running before a jump is executed. For basketball shots in which the player does not leave the ground, such as free-throws, the player's head motions will resemble those of a jump. In contrast however, there will not be a period of time where Ax and Ay both approach zero during these grounded shots. Once the beginning of a shot is detected, timing modules in the integrated circuit (713) will begin to measure the user's hang time. Although the beginning of a jump could be falsely detected, the firmware and the logic modules in the integrated circuit (711) comprise algorithms to account for such false detections. If a false detection is caught by the algorithms, the integrated circuit discards the detection, and returns to looking for patterns that could indicate the beginning of a jump, as shown by the flow chart in FIG. 5(h). If the detection was not a false detection, then the wearable electronic device (710) will subsequently analyze motion signals and perform calculations that yield statistics such as but not limited to the rotational velocity of the user while simultaneously looking for patterns that indicate the end of a shot. Once the end of the basketball shot is detected, the wearable electronic device (710) determines the hang time and calculates the jumping height achieved by the user. At this point, the algorithms still check to see if the jump was falsely detected. For example, the basketball player (800) may execute a pump-fake without actually shooting the basketball. The user (800) can then use specific pre-defined body motions to communicate to the wearable device that these shots should be discarded and ignored. For example, the user (800) can shake his/her head to communicate to the wearable device (710) that the previous shot should not be analyzed or counted. If the basketball shot was confirmed to be a true shot, the user (800) can communicate to the wearable electronic device (710) of the present invention whether he/she successfully made the basketball shot. For example, nodding of the head can indicate to the wearable device that the ball (802) successfully went through the basketball hoop (804). Using methods similar but not limited to these, the wearable electronic device (710) can count the number of shots taken and the number of shots made and can report the results using the electrical sound speaker (715) to the user (800) in real time. Other parameters such as jumping height, rotational velocity, rate of rotation, and hang time can also be reported using the electrical sound speaker (715) to the user (800) in real time. Data also can be stored in memory devices in the wearable electronic device (710) as records for future analysis.

While specific embodiments of the invention have been illustrated and described herein, it is realized that other modifications and changes will occur to those skilled in the art. It is therefore to be understood that the appended claims are intended to cover all modifications and changes as fall within the true spirit and scope of the invention.

What is claimed is:

1. A wearable electronic device that is designed to be worn on the head of a user comprising:
   a motion sensor;
   an integrated circuit that uses the outputs of the motion sensor to determine the hang time and/or jumping height of the user when the user executes a jump by detecting sudden accelerations in the face (Ax) and head (Ay) directions that indicate the beginning of a jump, and by detecting accelerations that indicate the end of a jump;
   an electrical sound speaker,
   wherein the wearable electronic device can report the jumping height and/or hang time to the user using the electrical sound speaker while the user is wearing the wearable electronic device.

2. The wearable electronic device in claim 1 can estimate and report the hang time of the user wearing the wearable electronic device when the accelerations detected by the motion sensor are not close to zero.

3. The wearable electronic device in claim 1 can estimate and report the rotational velocity and rate of rotation of the user wearing the wearable electronic device while the user is rotating when airborne.

4. The motion sensor in the wearable electronic device in claim 1 is an accelerometer that measures a three-dimensional acceleration vector, and outputs the three components of the acceleration vector along three measurement axes.

5. One of the measurement axes of the accelerometer in claim 4 is pointing in the face, or also known as the Ax, direction of the user wearing the wearable electronic device.

6. One of the measurement axes of the accelerometer in claim 4 is pointing in the head, or also known as the Ay, direction of the user wearing the wearable electronic device.

7. One of the measurement axes of the accelerometer in claim 4 is pointing in the side, or also known as the Az, direction of the user wearing the wearable electronic device.

8. The wearable electronic device in claim 1 can compare current jumping performances of the user wearing the wearable electronic device to jumping performances of a different user or to previous jumping performances of the same user and report the comparison results to the user by using the electrical sound speaker while the user is wearing the wearable electronic device.

9. The wearable electronic device in claim 8 can compare the current hang time of the user wearing the wearable electronic device to a hang time of a different user or to a hang time previously achieved by the same user and report the comparison results to the user by using the electrical sound speaker while the user is wearing the wearable electronic device.

10. The wearable electronic device in claim 8 can compare the current vertical jump height of the user wearing the wearable electronic device to a vertical jump height of a different user or to a vertical jump height previously achieved by the same user and report the comparison results to the user by using the electrical sound speaker while the user is wearing the wearable electronic device.

11. The wearable electronic device in claim 8 can compare the current rate of rotation of the user wearing the wearable electronic device to a rate of rotation of another user or to a rate of rotation previously achieved by the same user and report the comparison results to the user by using the electrical sound speaker while the user is wearing the wearable electronic device.

12. The wearable electronic device in claim 1 can report the number of jumps executed by the user wearing the wearable electronic device by using the electrical sound speaker while the user is wearing the wearable electronic device.

* * * * *